(12) United States Patent
Okura

(10) Patent No.: US 9,353,046 B2
(45) Date of Patent: May 31, 2016

(54) METHOD FOR PRODUCING ALKYLATED AROMATIC AMIDE DERIVATIVE

(71) Applicant: Mitsui Chemicals Agro, Inc., Tokyo (JP)

(72) Inventor: Hironari Okura, Mobara (JP)

(73) Assignee: Mitsui Chemicals Agro, Inc., Tokyo (JP)

( * ) Notice: Subject to any disclaimer, the term of this patent is extended or adjusted under 35 U.S.C. 154(b) by 0 days.

(21) Appl. No.: 14/389,934

(22) PCT Filed: Mar. 29, 2013

(86) PCT No.: PCT/JP2013/059695
§ 371 (c)(1),
(2) Date: Oct. 1, 2014

(87) PCT Pub. No.: WO2013/150988
PCT Pub. Date: Oct. 10, 2013

(65) Prior Publication Data
US 2015/0065721 A1    Mar. 5, 2015

(30) Foreign Application Priority Data

Apr. 3, 2012    (JP) ................................. 2012-085053

(51) Int. Cl.
*C07C 231/12* (2006.01)
*C07C 237/42* (2006.01)

(52) U.S. Cl.
CPC ............. *C07C 231/12* (2013.01); *C07C 237/42* (2013.01)

(58) Field of Classification Search
CPC ............................. C07C 231/12; C07C 237/42
USPC ........... 546/300, 316; 549/487; 564/154, 155, 564/157
See application file for complete search history.

(56) References Cited

U.S. PATENT DOCUMENTS

| | | |
|---|---|---|
| 2002/0032238 A1 | 3/2002 | Hauel |
| 2002/0198399 A1 | 12/2002 | Kohno |
| 2006/0089395 A1 | 4/2006 | Itai |
| 2009/0226422 A1 | 9/2009 | Chaudhary |
| 2009/0233962 A1 | 9/2009 | Nomura |

FOREIGN PATENT DOCUMENTS

| | | |
|---|---|---|
| CN | 101203484 | 6/2008 |
| CN | 102206172 A | 10/2011 |
| EP | 1911751 A1 | 4/2008 |
| EP | 2253617 A1 | 11/2010 |
| JP | 2001122836 A2 | 5/2001 |
| JP | 2003528806 | 9/2003 |
| JP | 2004502749 T2 | 1/2004 |
| JP | 2006306771 A2 | 11/2006 |

(Continued)

OTHER PUBLICATIONS

International Search Report dated Jul. 2, 2013 filed in PCT/JP2013/059695.

(Continued)

*Primary Examiner* — Jafar Parsa
*Assistant Examiner* — Amy C Bonaparte
(74) *Attorney, Agent, or Firm* — Rankin, Hill & Clark LLP

(57) ABSTRACT

Provided is a method for producing an aromatic amide derivative represented by Formula (4), the method including a process in which an aromatic amide derivative represented by Formula (1) and a haloalkyl compound represented by Formula (3) are reacted with each other in the presence of a base and a metal or metal salt. In the formulae, each of X and Y represents a hydrogen atom, a halogen atom, or the like. A represents a hydrogen atom, an alkyl group, a group represented by Formula (2), or the like. Each of $G^1$ and $G^2$ represents an oxygen atom or the like. $Q^1$ represents a phenyl group or the like. $R^1$ represents a hydrogen atom, an alkyl group, or the like. $Z^1$ represents a haloalkyl group or the like. Xa represents an iodine atom or the like. m represents a number of from 1 to 4, n1 represents a number from 1 to 5, and n2 represents a number of from 1 to 4.

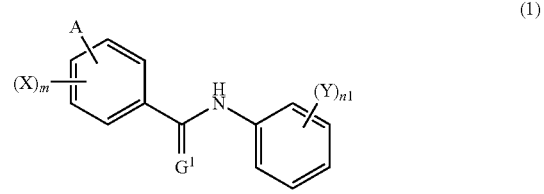

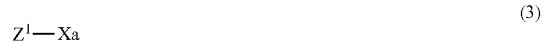

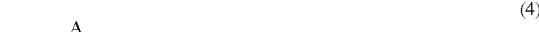

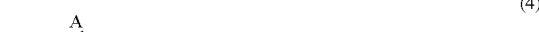

9 Claims, No Drawings

(56) References Cited

FOREIGN PATENT DOCUMENTS

| | | | |
|---|---|---|---|
| JP | 2010047478 | A2 | 3/2010 |
| JP | 201072101 | | 4/2010 |
| JP | 2011-153115 | | 8/2011 |
| WO | 0114339 | A2 | 3/2001 |
| WO | 03103654 | A1 | 12/2003 |
| WO | 2005073165 | A1 | 8/2005 |
| WO | 2006137376 | A1 | 12/2006 |
| WO | 2008075465 | A1 | 6/2008 |
| WO | 2010018714 | A1 | 2/2010 |
| WO | 2010133312 | A1 | 11/2010 |
| WO | 2011118759 | A1 | 9/2011 |

OTHER PUBLICATIONS

Fuchikami T. et al. "Direct Perfluoroalkylation of Functionalized Benzenes With Perfluoroalkyl Halides and Copper Bronze," Journal of Fluorine Chemistry, 1983, vol. 22, Issue 6, pp. 541-556.

Shivaputra Patil et al. "Synthesis and biological evaluation of novel 5(H)-phenanthridin-6-ones, 5(H)-phenanthridin-6-one diketo acid, and polycyclic aromatic diketo acid analogs as new HIV-1 integrase inhibitors," Bioorganic & Medicinal Chemistry, 15(3), pp. 1212-1228, 2007.

Grammaticakis,P. "Preparation and ultraviolet absorption of some m-(amino- and m-(acylaminobenzoyl)aryl amines," Comptes Rendus des Seances de l'Academie des Sciences, Serie C: Sciences Chimiques, 1966, vol. 263, No. 21, pp. 1306-1309.

"Shin Jikken Kagaku Koza 14 Yuki Kagobutsu no Gosei to Hanno I," 1st edition, vol. 14, 1977, p. 62; Partial English Translation thereof.

Extended European Search Report dated Sep. 16, 2015 issued in the corresponding European patent application No. 13773111.3.

Chinese Office Action dated Jun. 25, 2015 issued in the corresponding Chinese patent application No. 201380018859.9; Partial English translation included.

Japanese Office Action dated Jun. 16, 2015 issued in the corresponding Japanese patent application No. 2014-509140 and English translation thereof.

Kuroda, Noritaka. et al., "Further Development of Robust Workup Process for Solution-Phase High-Throughput Library Synthesis To Address Environmental and Sample Tracking Issues," J. Comb. Chem., 2006, 8, pp. 505-512.; Japanese Office Action.

Japanese Office Action dated Jan. 5, 2016 issued in the corresponding Japanese patent application No. 2014-509140.

METHOD FOR PRODUCING ALKYLATED AROMATIC AMIDE DERIVATIVE

TECHNICAL FIELD

The present invention relates to a method for producing an alkylated aromatic amide derivative.

BACKGROUND ART

International Publication WO 2005/73165, International Publication WO 2006/137376, and International Publication WO 2010/18714 disclose various compounds as amide derivatives having pest control effects, and disclose that an amide derivative having a perfluoroalkylated phenyl group is useful in the production of the amide derivative.

As a method for producing an aniline having a perfluoroalkylated phenyl group, a production method in which a perfluoroalkyl halogen compound is reacted in the presence of a reducing agent is known (see, for example, Japanese Patent Application Laid-Open (JP-A) No. 2001-122836). Further, as a method for producing an amide derivative having a perfluoroalkylated phenyl group, the method described in the Journal of Fluorine Chemistry 22, 541-556, 1983, is known.

Further, there are some known methods of halogenating an amide compound having an aromatic ring having an electron-withdrawing group (see, for example, Bioorganic & Medicinal Chemistry, 15 (3), 1212-1228, 2007); however, a method of halogenating an amide derivative having a perfluoroalkylated phenyl group is not known.

SUMMARY OF INVENTION

Technical Problem

JP-A No. 2001-122836 describes only the case of aniline, and does not specifically disclose an amide compound. The present inventors attempted to perfluoroalkylate an amide compound using the method described in JP-A No. 2001-122836, but the reaction was unsuccessful.

Further, in the method described in the Journal of Fluorine Chemistry 22, 541-556, 1983, a high temperature is needed for the reaction, and therefore, the method cannot be applied to a perfluoroalkyl halogen compound having a low boiling point, thereby introducing constraints. In addition, since the yield of the product and the reaction selectivity are low, this method holds little promise for practical application.

With the method described in Bioorganic & Medicinal Chemistry, 15 (3), 1212-1228, 2007, the yield of halogenation is low, and when the present inventors performed a halogenating reaction of an amide compound having an electron-withdrawing group in accordance with the method described in Non-Patent Document 2, the yield of the product was low. Consequently, in present circumstances, knowledge suggesting a reaction method by which an amide derivative having a perfluoroalkylated phenyl group is halogenated and which is usable in industrial production, remains elusive.

The invention has been made in view of the foregoing problems, and aims to provide a short-step and industrially usable method for producing an aromatic amide derivative having an alkyl group, and to provide a production intermediate useful in the production method.

Solution to Problem

The present inventors have conducted intensive research in order to address the foregoing problems and, as a result, they have found a novel method for producing an aromatic amide derivative having an alkyl group (preferably, a perfluoroalkyl group) and a novel and useful intermediate that is usable in the production method, and further, they have found that the useful intermediate can be selectively halogenated. As a result, they have found a method for easily producing a novel insecticide having high insecticidal activity, whereby the present invention has been accomplished.

Namely the invention is as follows.

<1> A method for producing an alkylated aromatic amide derivative represented by the following Formula (4), the method including a process of allowing an aromatic amide derivative represented by the following Formula (1) and a haloalkyl compound represented by the following formula (3) to react with each other in the presence of a base and a metal or metal salt:

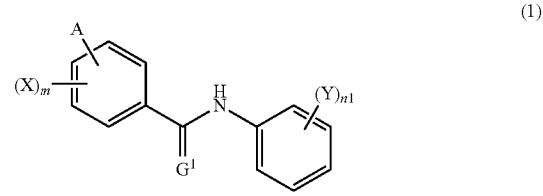

wherein, in Formula (1), each X independently represents a hydrogen atom, a halogen atom, a nitro group, a cyano group, a C1-C4 alkoxy group, or a dimethylamino group; m represents an integer from 1 to 4, and n1 represents an integer from 1 to 5; $G^1$ represents an oxygen atom or a sulfur atom; each of Y independently represents a hydrogen atom, a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, or an acetylamino group;

A represents a hydrogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, a C1-C4 alkylaminocarbonyl group, a methylsulfinyl C1-C4-alkylamino-carbonyl group, a methylsulfonyl C1-C4-alkylamino-carbonyl group, an acetylamino group, or an unsubstituted phenyl group, or a phenyl group having one or more substituents, which may be the same or different, selected from the group consisting of a halogen atom, a C1-C6 alkyl group, a C1-C6 haloalkyl group, a C2-C4 alkoxy group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group, or an unsubstituted heterocyclic group, or a heterocyclic group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group, or a group represented by the following Formula (2):

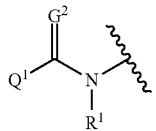

(2)

wherein, in Formula (2), $G^2$ represents an oxygen atom or a sulfur atom;

$R^1$ represents a hydrogen atom, a C1-C6 alkyl group, or a C1-C6 haloalkyl group; and $Q^1$ represents a C1-C6 alkyl group, a C1-C6 haloalkyl group, or an unsubstituted phenyl group, or a phenyl group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group, or an unsubstituted heterocyclic group, or a heterocyclic group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group; and the heterocyclic group represents a pyridyl group, a pyridin-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group, or a tetrazolyl group:

$$Z^1-Xa \qquad (3)$$

wherein, in Formula (3), $Z^1$ represents a C1-C6 alkyl group or a C1-C6 haloalkyl group; and Xa represents an iodine atom or a bromine atom:

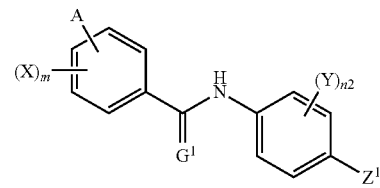

(4)

wherein, in Formula (4), n2 represents an integer from 1 to 4; $Z^1$ has the same definition as $Z^1$ in Formula (3), and X, m, $G^1$, Y, and A have the same definitions as X, m, $G^1$, Y, and A in Formula (1), respectively.

<2> The production method according to <1>, wherein the aromatic amide derivative represented by Formula (1) is an aromatic amide derivative represented by the following Formula (5), and the alkylated aromatic amide derivative represented by Formula (4) is an alkylated aromatic amide derivative represented by the following Formula (6):

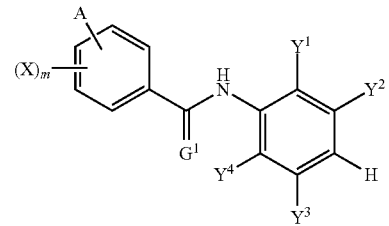

(5)

wherein, in Formula (5), each of $Y^1$, $Y^2$, $Y^3$, and $Y^4$ independently represents a hydrogen atom, a halogen atom, a C1-C6 alkyl group, a C1-C6 haloalkyl group, a C1-C4 alkylthio group, a C1-C4 haloalkylthio group, a C1-C4 alkylsulfinyl group, a C1-C4 haloalkylsulfinyl group, a C1-C4 alkylsulfonyl group, or a C1-C4 haloalkylsulfonyl group; and X, m, $G^1$, and A have the same definitions as X, m, $G^1$, and A in Formula (1), respectively.

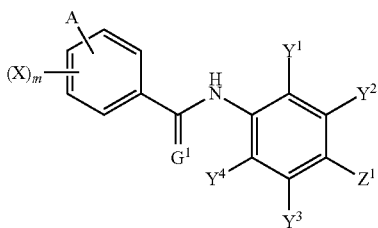

(6)

wherein in Formula (6), $Z^1$ has the same definition as $Z^1$ in Formula (3); and $Y^1$, $Y^2$, $Y^3$, $Y^4$, X, m, $G^1$, and A have the same definitions as $Y^1$, $Y^2$, $Y^3$, $Y^4$, X, m, $G^1$, and A in Formula (5), respectively.

<3> The production method according to <2>, wherein the aromatic amide derivative represented by Formula (5) is an aromatic amide derivative represented by the following Formula (7), and the alkylated aromatic amide derivative represented by Formula (6) is an alkylated aromatic amide derivative represented by the following Formula (8):

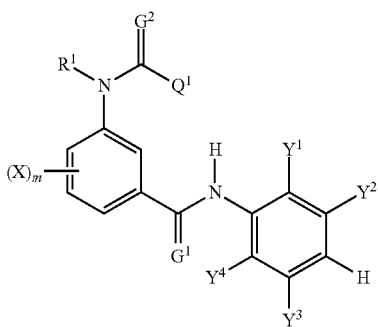

(7)

wherein, in Formula (7), $G^2$, $Q^1$, and $R^1$ have the same definitions as $G^2$, $Q^1$ and $R^1$ in Formula (2), respectively; and X, m, $G^1$, $Y^1$, $Y^2$, $Y^3$, and $Y^4$ have the same definitions as X, m, $G^1$, $Y^1$, $Y^2$, $Y^3$, and $Y^4$ in Formula (5), respectively;

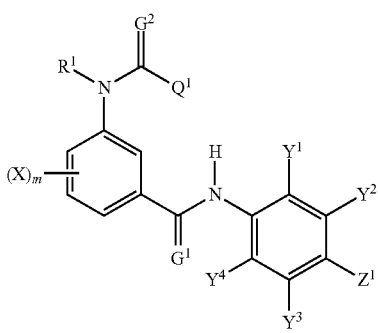

(8)

wherein, in Formula (8), $Z^1$ has the same definition as $Z^1$ in Formula (3); and $Y^1$, $Y^2$, $Y^3$, $Y^4$, X, m, $G^1$, $G^2$, $Q^1$, and $R^1$ have the same definitions as $Y^1$, $Y^2$, $Y^3$, $Y^4$, X, m, $G^1$, $G^2$, $Q^1$, and $R^1$ in Formula (7), respectively.

<4> A method for producing a halogenated aromatic amide derivative represented by the following Formula (10), the method including a process of allowing an aromatic amide derivative represented by the following Formula (7a) and a haloalkyl compound represented by the following formula (3) to react with each other in the presence of a base and a metal or metal salt, to obtain an alkylated aromatic amide derivative represented by the following Formula (9), and a process of halogenating the alkylated aromatic amide derivative represented by Formula (9) under a basic condition:

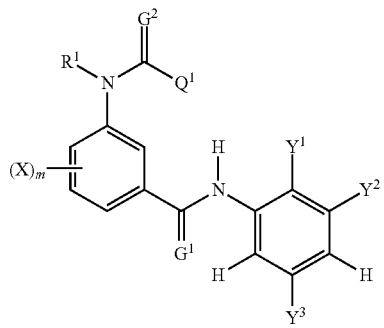

(7a)

wherein in Formula (7a), each X independently represents a hydrogen atom, a halogen atom, a nitro group, a cyano group a C1-C4 alkoxy group, or a dimethylamino group. m represents an integer from 1 to 4;

each of $G^1$ and $G^2$ independently represents an oxygen atom or a sulfur atom;

each of $Y^1$, $Y^2$, and $Y^3$ independently represents a hydrogen atom, a halogen atom, a C1-C6 alkyl group, a C1-C6 haloalkyl group, a C1-C4 alkylthio group, a C1-C4 haloalkylthio group, a C1-C4 alkylsulfinyl group, a C1-C4 haloalkylsulfinyl group, a C1-C4 alkylsulfonyl group, or a C1-C4 haloalkylsulfonyl group;

$R^1$ represents a hydrogen atom, a C1-C6 alkyl group, or a C1-C6 haloalkyl group;

$Q^1$ represents a C1-C6 alkyl group, a C1-C6 haloalkyl group, or an unsubstituted phenyl group, or a phenyl group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group, or an unsubstituted heterocyclic group, or a heterocyclic group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group; and the heterocyclic group represents a pyridyl group, a pyridin-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group, or a tetrazolyl group:

$Z^1$—Xa    (3)

wherein, in Formula (3), $Z^1$ represents a C1-C6 alkyl group or a C1-C6 haloalkyl group; Xa represents an iodine atom or a bromine atoms:

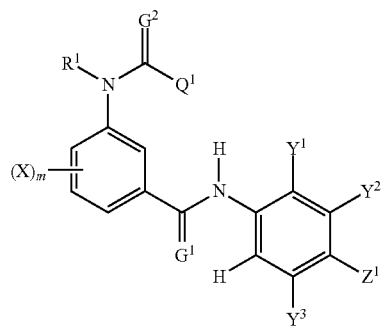

(9)

wherein, in Formula (9), $Z^1$ has the same definition as $Z^1$ in Formula (3); and X, m, $G^1$, $G^2$, $Q^1$, $R^1$, $Y^1$, $Y^2$, and $Y^3$ have the same definitions as X, m, $G^1$, $G^2$, $Q^1$, $R^1$, $Y^1$, $Y^2$, and $Y^3$ in Formula (7a), respectively;

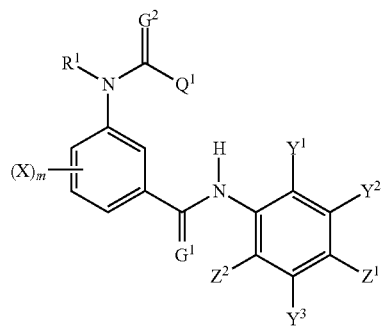

(10)

wherein, in Formula (10), $Z^2$ represents a halogen atom; and X, m, $G^1$, $G^2$, $Q^1$, $R^1$, $Y^1$, $Y^2$, $Y^3$, and $Z^1$ have the same definitions as X, m, $G^1$, $G^2$, $Q^1$, $R^1$, $Y^1$, $Y^2$, $Y^3$, and $Z^1$ in Formula (9), respectively.

<4A> A method for producing a halogenated aromatic amide derivative represented by the following Formula (10), the method including:

a process of obtaining an alkylated aromatic amide derivative represented by Formula (6) by the production method according to <2>, and a process of halogenating the alkylated aromatic amide derivative represented by Formula (6) under a basic condition:

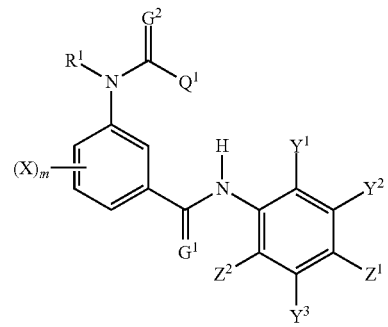

(10)

wherein, in Formula (10), $Z^2$ represents a halogen atom; X, m, $G^1$, $Y^1$, $Y^2$, $Y^3$, and $Z^1$ have the same definitions as X, m, $G^1$, $G^2$, $Q^1$, $R^1$, $Y^1$, $Y^2$, $Y^3$, and $Z^1$ in Formula (6), respectively; and $G^2$, $Q^1$, and $R^1$ have the same definitions as $G^2$, $Q^1$, and $R^1$ in Formula (2), respectively; and wherein, in Formula (6), A is represented by Formula (2), and $Y^4$ represents a hydrogen atom.

<4B> A method for producing a halogenated aromatic amide derivative represented by the following Formula (10), the method including:

a process of obtaining an alkylated aromatic amide derivative represented by Formula (8) by the production method according to <3>, and a process of halogenating the alkylated aromatic amide derivative represented by Formula (8) under a basic condition:

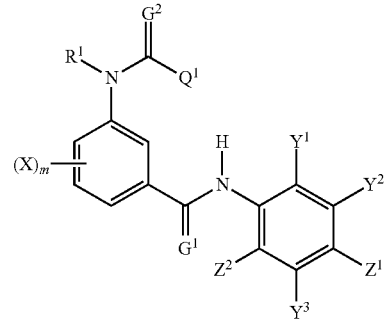

(10)

wherein in Formula (10), $Z^2$ represents a halogen atom; and X, m, $G^1$, $G^2$, $Q^1$, $R^1$, $Y^1$, $Y^2$, $Y^3$, and $Z^1$ have the same definitions as X, m, $G^1$, $G^2$, $Q^1$, $R^1$, $Y^1$, $Y^2$, $Y^3$, and $Z^1$ in Formula (8), respectively; and wherein, in Formula (8), $Y^4$ represents a hydrogen atom.

<5> An aromatic amide derivative represented by the following Formula (7):

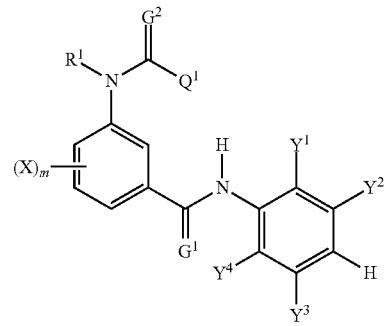

(7)

wherein, in Formula (7), each X independently represents a hydrogen atom, a halogen atom, a nitro group, a cyano group, a C1-C4 alkoxy group, or a dimethylamino group;

m represents an integer from 1 to 4;

each of $G^1$ and $G^2$ independently represents an oxygen atom or a sulfur atom;

each of $Y^1$, $Y^2$, $Y^3$, and $Y^4$ independently represents a hydrogen atom, a halogen atom, a C1-C6 alkyl group, a C1-C6 haloalkyl group, a C1-C4 alkylthio group, a C1-C4 haloalkylthio group, a C1-C4 alkylsulfinyl group, a C1-C4 haloalkylsulfinyl group, a C1-C4 alkylsulfonyl group, or a C1-C4 haloalkylsulfonyl group;

$R^1$ represents a hydrogen atom, a C1-C6 alkyl group, or a C1-C6 haloalkyl group;

$Q^1$ represents a C1-C6 alkyl group, a C1-C6 haloalkyl group, or an unsubstituted phenyl group, or a phenyl group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group, or an unsubstituted heterocyclic group, or a heterocyclic group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group; and the heterocyclic group represents a pyridyl group, a pyridin-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group, or a tetrazolyl group.

<6> An alkylated aromatic amide derivative represented by the following Formula (9):

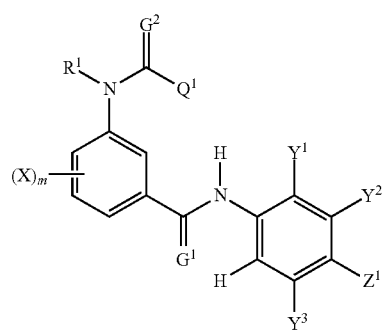

(9)

wherein, in Formula (9), each X independently represents a hydrogen atom, a halogen atom, a nitro group, a cyano group, a C1-C4 alkoxy group, or a dimethylamino group;

m represents an integer from 1 to 4;

each of $G^1$ and $G^2$ independently represents an oxygen atom or a sulfur atom;

each of $Y^1$, $Y^2$, and $Y^3$ independently represents a hydrogen atom, a halogen atom, a C1-C6 alkyl group, a C1-C6 haloalkyl group, a C1-C4 alkylthio group, a C1-C4 haloalkylthio group, a C1-C4 alkylsulfinyl group, a C1-C4 haloalkylsulfinyl group, a C1-C4 alkylsulfonyl group, or a C1-C4 haloalkylsulfonyl group;

$Z^1$ represents a C1-C6 alkyl group or a C1-C6 haloalkyl group;

$R^1$ represents a hydrogen atom, a C1-C6 alkyl group, or a C1-C6 haloalkyl group;

$Q^1$ represents a C1-C6 alkyl group, a C1-C6 haloalkyl group, or an unsubstituted phenyl group, or a phenyl group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group, or an unsubstituted heterocyclic group, or a heterocyclic group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group; and the heterocyclic group represents a pyridyl group, a pyridin-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group, or a tetrazolyl group.

<7> The alkylated aromatic amide derivative according to <6>, wherein, in Formula (9), $Y^1$ represents a C1-C2 haloalkyl group, each of $Y^2$ and $Y^3$ represents a hydrogen atom, $Z^1$ represents a C1-C6 haloalkyl group, and X represents a halogen atom.

Advantageous Effects of Invention

According to the invention, a short-step and industrially usable method for producing an aromatic amide derivative having an alkyl group can be provided. Further, a production intermediate that is useful in the production method can be provided.

DESCRIPTION OF EMBODIMENTS

In this specification, the term "process" includes not only an independent process, but also a case in which the process cannot be clearly distinguished from another process, as long as the predetermined action of the process is achieved. Further, a numerical range expressed using "to" denotes a range including numerical values described in front of and behind "to", as the minimum value and the maximum value, respectively.

The terms used in the formulae described in this specification have the definitions as described below, respectively, on the basis of their definitions.

"Halogen atom" represents a fluorine atom, a chlorine atom, a bromine atom, or an iodine atom. The term "n-" means "normal", "i-" means "iso", "s-" means "secondary", and "t-" means "tertiary".

Concerning the expression "Ca-Cb (wherein each of a and b represents an integer of 1 or more)", for example, "C1-C3" means that the number of carbon atom is from 1 to 3 carbon, "C2-C6" means that the number of carbon atom is from 2 to 6, and "C1-C4" means that the number of carbon atom is from 1 to 4.

"C1-C3 alkyl group" represents a straight chain or branched alkyl group having from 1 to 3 carbon atoms, for example, methyl, ethyl, n-propyl, i-propyl, or the like. "C1-C4 alkyl group" represents a straight chain or branched alkyl group having from 1 to 4 carbon atoms, for example, n-butyl, s-butyl, i-butyl, t-butyl, or the like, in addition to the "C1-C3 alkyl group". "C1-C6 alkyl group" represents a straight chain or branched alkyl group having from 1 to 6 carbon atoms, for example, n-pentyl, 2-pentyl, 3-pentyl, neopentyl, n-hexyl, 2-hexyl, 4-methyl-2-pentyl, 3-methyl-n-pentyl, or the like, in addition to the "C1-C4 alkyl group".

"C1-C6 haloalkyl group" represents a straight chain or branched alkyl group having from 1 to 6 carbon atoms and being substituted with one or more halogen atoms which may be the same or different, for example, monofluoromethyl, difluoromethyl, trifluoromethyl, monochloromethyl, dichloromethyl, trichloromethyl, monobromomethyl, dibromomethyl, tribromomethyl, 1-fluoroethyl, 2-fluoroethyl, 2,2-difluoroethyl, 2,2,2-trifluoroethyl, 1-chloroethyl, 2-chloroethyl, 2,2-dichloroethyl, 2,2,2-trichloroethyl, 1-bromoethyl, 2-bromoethyl, 2,2-dibromoethyl, 2,2,2-tribromoethyl, 2-iodoethyl, pentafluoroethyl, 3-fluoro-n-propyl, 3-chloro-n-propyl, 3-bromo-n-propyl, 1,3-difluoro-2-propyl, 1,3-dichloro-2-propyl, 1,1,1-trifluoro-2-propyl, 1-chloro-3-fluoro-2-propyl, 1,1,1,3,3,3-hexafluoro-2-propyl, 1,1,1,3,3,3-hexafluoro-2-chloro-2-propyl, 2,2,3,3,3-pentafluoro-n-propyl, heptafluoro-i-propyl, heptafluoro-n-propyl, 4-fluoro-n-butyl, nonafluoro-n-butyl, nonafluoro-2-butyl, nonafluoro-i-butyl, undecafluoro-n-pentyl, undecafluoro-i-pentyl, undecafluoroneopentyl, tridecafluoro-n-hexyl, tridecafluoro-n-hexyl, or the like.

"C2-C4 alkenyl group" represents an alkenyl group having from 2 to 4 carbon atoms and a double bond in the carbon chain, for example, vinyl, allyl, 2-butenyl, 3-butenyl, or the like. "C2-C4 haloalkenyl group" represents a straight chain or branched alkenyl group having from 2 to 4 carbon atoms and a double bond in the carbon chain, and being substituted with one or more halogen atoms which may be the same or different, for example, 3,3-difluoro-2-propenyl, 3,3-dichloro-2-propenyl, 3,3-dibromo-2-propenyl, 2,3-dibromo-2-propenyl, 4,4-difluoro-3-butenyl, 3,4,4-tribromo-3-butenyl, or the like.

"C2-C4 alkynyl group" represents a straight chain or branched alkynyl group having from 2 to 4 carbon atoms and a triple bond in the carbon chain, for example, propargyl, 1-butyn-3-yl, 1-butyn-3-methyl-3-yl, or the like. "C2-C4 haloalkynyl group" represents, for example, a straight chain or branched alkenyl group having from 2 to 4 carbon atoms and a triple bond in the carbon chain, and being substituted with one or more halogen atoms which may be the same or different.

"C3-C6 cycloalkyl group" represents a cycloalkyl group having from 3 to 6 carbon atoms and a cyclic structure, for example, cyclopropyl, cyclobutyl, cyclopentyl, 2-methylcyclopentyl, 3-methylcyclopentyl, cyclohexyl, or the like. "C3-C6 halocycloalkyl group" represents a cycloalkyl group having from 3 to 6 carbon atoms and a cyclic structure, and being substituted with one or more halogen atoms which may be the same or different, for example, 2,2,3,3-tetrafluorocyclobutyl, 2-chlorocyclohexyl, 4-chlorocyclohexyl, or the like.

"C1-C4 alkoxy group" represents a straight chain or branched alkoxy group having from 1 to 3 carbon atoms, for example, methoxy, ethoxy, n-propyloxy, isopropyloxy, n-butyloxy, i-butyloxy, or the like. "C1-C4 haloalkoxy group" represents a straight chain or branched haloalkoxy group having from 1 to 4 carbon atoms and being substituted with one or more halogen atoms which may be the same or different, for example, trifluoromethoxy, 1,1,1,3,3,3-hexafluoro-2-propyloxy, 2,2,2-trifluoroethoxy, 2-chloroethoxy, 3-fluoro-n-propyloxy, 1,1,1,3,3,4,4,4-octafluoro-2-butyloxy, or the like.

"C1-C4 alkylthio group" represents a straight chain, branched, or cyclic alkylthio group having from 1 to 4 carbon atoms, for example, methylthio, ethylthio, n-propylthio, i-propylthio, cyclopropylthio, n-butylthio, i-butylthio, s-butylthio, t-butylthio, cyclopropylmethylthio, or the like. "C1-C4 haloalkylthio group" represents a straight chain or a branched alkylthio group having from 1 to 4 carbon atoms and being substituted with one or more halogen atoms which may be the same or different, for example, trifluoromethylthio, pentafluoroethylthio, 2,2,2-trifluoroethylthio, heptafluoro-n-propylthio, heptafluoro-i-propylthio, nonafluoro-n-butylthio, nonafluoro-i-butylthio, nonafluoro-s-butylthio, 4,4,4-trifluoro-n-butylthio, or the like.

"C1-C4 alkylsulfinyl group" represents a straight chain, branched, or cyclic alkylsulfinyl group having from 1 to 4 carbon atoms, for example, methylsulfinyl, ethylsulfinyl, n-propylsulfinyl, i-propylsulfinyl, cyclopropylsulfinyl, n-butylsulfinyl, i-butylsulfinyl, or the like. "C1-C4 haloalkylsulfinyl group" represents a straight chain or branched alkylsulfinyl group having from 1 to 4 carbon atoms and being substituted with one or more halogen atoms which may be the same of different, for example, trifluoromethylsulfinyl, pentafluoroethylsulfinyl, 2,2,2-trifluoroethylsulfinyl, heptafluoro-n-propylsulfinyl, heptafluoro-i-propylsulfinyl, nonafluoro-n-butylsulfinyl, nonafluoro-i-butylsulfinyl, nonafluoro-s-butylsulfinyl, 4,4,4-trifluoro-n-butylsulfinyl, or the like.

"C1-C4 alkylsulfonyl group" represents a straight chain, branched, or cyclic alkylsulfonyl group having from 1 to 4 carbon atoms, for example, methylsulfonyl, ethylsulfonyl, n-propylsulfonyl, i-propylsulfonyl, cyclopropylsulfonyl, n-butylsulfonyl, i-butylsulfonyl, or the like. "C1-C4 haloalkylsulfonyl group" represents a straight chain or branched alkylsulfonyl group having from 1 to 4 carbon atoms and being substituted with one or more halogen atoms which may be the same or different, for example, trifluoromethylsulfonyl, pentafluoroethylsulfonyl, 2,2,2-trifluoroethylsulfonyl, heptafluoro-n-propylsulfonyl, heptafluoro-i-propylsulfonyl, nonafluoro-n-butylsulfonyl, nonafluoro-s-butylsulfonyl, or the like.

"Arylsulfonyl group" represents an arylsulfonyl group having from 6 to 14 carbon atoms and an aromatic ring, for example, phenylsulfonyl, p-toluenesulfonyl, 1-naphthylsulfonyl, 2-naphthylsulfonyl, anthrylsulfonyl, phenanthrylsulfonyl, acenaphthylenylsulfonyl, or the like.

"C1-C4 alkylamino group" represents a straight chain, branched, or cyclic alkylamino group having from 1 to 4 carbon atoms, for example, methylamino, ethylamino, n-propylamino, i-propylamino, n-butylamino, cyclopropylamino, or the like. "Di-C1-C4-alkylamino group" represents an amino group substituted with two straight chain or branched alkyl groups each having from 1 to 4 carbon atoms, which may be the same or different, for example, dimethylamino, diethylamino, N-ethyl-N-methylamino, or the like.

"C1-C4 alkylcarbonyl group" represents a straight chain, branched, or cyclic alkylcarbonyl group having from 1 to 4 carbon atoms, for example, formyl, acetyl, propionyl, isopropylcarbonyl, cyclopropylcarbonyl, or the like. "C1-C4 haloalkylcarbonyl group" represents a straight chain or branched alkylcarbonyl group having from 1 to 4 carbon atoms and being substituted with one or more halogen atoms which may be the same or different, for example, fluoroacetyl, difluoroacetyl, trifluoroacetyl, chloroacetyl, dichloroacetyl, trichloroacetyl, bromoacetyl, iodoacetyl, 3,3,3-trifluoropropionyl, 2,2,3,3,3-pentafluoropropionyl, or the like.

"C1-C4 alkylcarbonyloxy group" represents a straight chain or branched alkylcarbonyloxy group having from 1 to 4 carbon atoms, for example, acetoxy, propionyloxy, or the like. "C1-C4 alkoxycarbonyl group" represents a straight chain or branched alkoxycarbonyl group having from 1 to 4 carbon atoms, for example, methoxycarbonyl, ethoxycarbonyl, isopropyloxycarbonyl, or the like.

"C1-C6 perfluoroalkyl group" represents a straight chain or branched alkyl group having from 1 to 4 carbon atoms and being completely substituted with fluorine atoms, for example, trifluoromethyl, pentafluoroethyl, heptafluoro-n-propyl, heptafluoro-i-propyl, nonafluoro-n-butyl, nonafluoro-2-butyl, nonafluoro-i-butyl, perfluoro-n-pentyl, perfluoro-n-hexyl, or the like.

"C1-C6 perfluoroalkylthio group" represents a straight chain or branched alkylthio group having from 1 to 6 carbon atoms and being completely substituted with fluorine atoms, for example, trifluoromethylthio, pentafluoroethylthio, heptafluoro-n-propylthio, heptafluoro-i-propylthio, nonafluoro-n-butylthio, nonafluoro-2-butylthio, nonafluoro-i-butylthio, perfluoro-n-pentylthio, perfluoro-n-hexylthio, or the like.

"C1-C6 perfluoroalkylsulfinyl group" represents a straight chain or branched alkylsulfinyl group having from 1 to 6 carbon atoms and being completely substituted with fluorine atoms, for example, trifluoromethylsulfinyl, pentafluoroethylsulfinyl, heptafluoro-n-propylsulfinyl, heptafluoro-i-propylsulfinyl, nonafluoro-n-butylsulfinyl, nonafluoro-2-butylsulfinyl, nonafluoro-i-butylsulfinyl, perfluoro-n-pentylsulfinyl, perfluoro-n-hexylsulfinyl, or the like.

"C1-C6 perfluoroalkylsulfonyl group" represents a straight chain or branched alkylsulfonyl group having from 1 to 6 carbon atoms and being completely substituted with fluorine atoms, for example, trifluoromethylsulfonyl, pentafluoroethylsulfonyl, heptafluoro-n-propylsulfonyl, heptafluoro-i-propylsulfonyl, nonafluoro-n-butylsulfonyl, nonafluoro-2-butylsulfonyl, nonafluoro-i-butylsulfonyl, perfluoro-n-pentylsulfonyl, perfluoro-n-hexylsulfonyl, or the like.

In the invention, some of the compounds represented by Formula (1), Formula (3), or the like may include one or two or more chiral carbon atoms or chiral centers in their structural formulae, and thus, may have two or more optical isomers. The scope of the invention encompasses of the individual optical isomers and any mixture containing such optical isomers in any proportion.

Further, the compound represented by Formula (1), Formula (3), or the like in the invention may have two or more geometrical isomers originating from carbon-carbon double bond(s) in their structural formulae. The scope of the invention also encompasses any mixture containing such geometrical isomers in any proportion.

The method for producing an alkylated aromatic amide derivative represented by the following Formula (4) of the invention includes a process of allowing an aromatic amide derivative represented by the following Formula (1) and a haloalkyl compound represented by the following Formula (3) to react with each other in the presence of a base and a metal or metal salt. The production method may further include other process(es), if necessary.

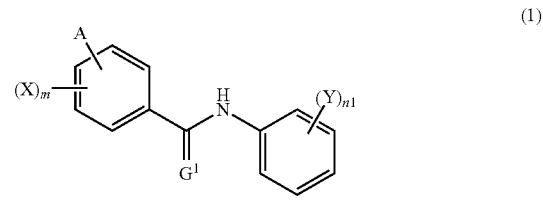

(1)

(3)

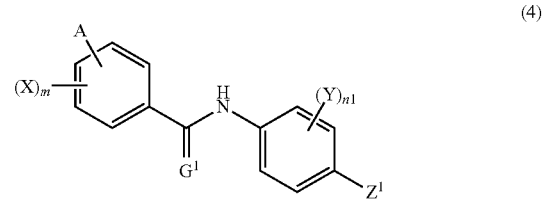

(4)

In Formula (1), each X independently represents a hydrogen atom, a halogen atom, a nitro group, a cyano group, a C1-C4 alkoxy group, or a dimethylamino group. m represents an integer from 1 to 4, and n1 represent an integer from 1 to 5. In a case in which plural Xs exist, each of Xs may be the same or different.

$G^1$ represents an oxygen atom or a sulfur atom.

Each Y independently represents a hydrogen atom, a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, or an acetylamino group.

In a case in which plural Ys exist, each of Ys may be the same or different.

A represents a hydrogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, a C1-C4 alkylaminocarbonyl group, a methylsulfinyl C1-C4-alkylamino-carbonyl group, a methylsulfonyl C1-C4-alkylamino-carbonyl group, an acetylamino group, an unsubstituted phenyl group, or a phenyl group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group, an unsubstituted heterocyclic group, or a heterocyclic group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group, or a group represented by the following Formula (2).

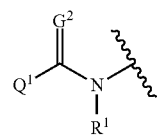

(2)

In Formula (2), $G^2$ represents an oxygen atom or a sulfur atom.

$R^1$ represents a hydrogen atom, a C1-C6 alkyl group, or a C1-C6 haloalkyl group.

$Q^1$ represents a C1-C6 alkyl group, a C1-C6 haloalkyl group, an unsubstituted phenyl group, or a phenyl group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an aryl sulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group, or an unsubstituted heterocyclic group, or a heterocyclic group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyl group, a C1-C4 alkylcarbonyloxy group, a C1-C4 alkoxycarbonyl group, an acetylamino group, and a phenyl group.

Note that, the heterocyclic group in Formula (1) represents a pyridyl group, a pyridin-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group, or a tetrazolyl group.

The aromatic amide derivative represented by Formula (1) in the invention is a particularly useful production intermediate in producing the compound represented by Formula (10), which is useful as an insecticide.

In Formula (1), the substituent X is a hydrogen atom, a halogen atom, a nitro group, a cyano group, a C1-C4 alkoxy group, or a dimethylamino group, and preferably a halogen atom, a nitro group, a cyano group, or a dimethylamino group. m is an integer from 1 to 4, and more preferably an integer from 1 to 3.

Further, the substituent A preferably represents a C1-C6 alkyl group, a C1-C6 haloalkyl group, a C1-C4 alkoxy group, a C1-C4 haloalkoxy group, a phenyl group having a substituent, a halogen atom, a nitro group, a cyano group, or a group represented by Formula (2) above. The substituent $G^2$ in Formula (2) is an oxygen atom or a sulfur atom, and preferably an oxygen atom. The substituent $Q^1$ is preferably an unsubstituted phenyl group, a phenyl group having a substituent, an unsubstituted heterocyclic group, a heterocyclic group having a substituent, a C1-C6 alkyl group, a C1-C6 haloalkyl group, a C1-C4 alkoxy group, or a C1-C4 haloalkoxy group.

The substituent $R^1$ is preferably a hydrogen atom, a C1-C6 alkyl group, or a C1-C6 haloalkyl group. The substituent Y is preferably a hydrogen atom, a halogen atom, a C1-C6 alkyl group, a C1-C6 haloalkyl group, a C1-C4 alkylthio group, a C1-C4 haloalkylthio group, a C1-C4 alkylsulfinyl group, a C1-C4 haloalkylsulfinyl group, a C1-C4 alkylsulfonyl group, or a C1-C4 haloalkylsulfonyl group. n1 is an integer from 1 to 5, and more preferably an integer from 1 to 3. The aromatic amide derivative represented by Formula (1) above is preferably an aromatic amide derivative represented by the following Formula (5), and more preferably an aromatic amide derivative represented by the following Formula (7).

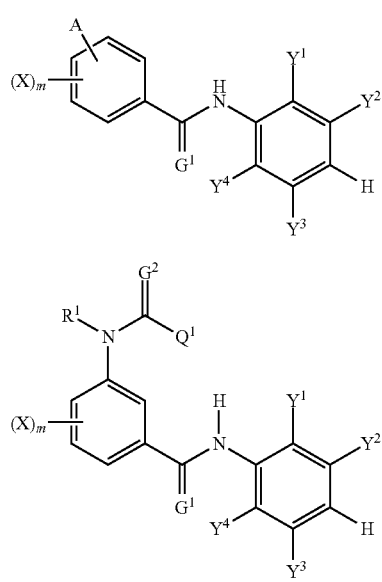

In Formula (5), each of $Y^1$, $Y^2$, $Y^3$, and $Y^4$ independently represents a hydrogen atom, a halogen atom, a C1-C6 alkyl group, a C1-C6 haloalkyl group, a C1-C4 alkylthio group, a C1-C4 haloalkylthio group, a C1-C4 alkylsulfinyl group, a C1-C4 haloalkylsulfinyl group, a C1-C4 alkylsulfonyl group, or a C1-C4 haloalkylsulfonyl group. X, m, $G^1$, and A have the same definitions as X, m, $G^1$, and A in Formula (1) above, respectively.

It is preferable that each of $Y^1$, $Y^2$, $Y^3$, and $Y^4$ in Formula (5) independently represents a hydrogen atom, a halogen atom, a C1-C6 haloalkyl group, a C1-C4 haloalkylthio group, a C1-C4 haloalkylsulfinyl group, or a C1-C4 haloalkylsulfonyl group.

$G^2$, $Q^1$, and $R^1$ in Formula (7) have the same definitions as $G^2$, $Q^1$ and $R^1$ in Formula (2) above, respectively. X, m, $G^1$, $Y^1$, $Y^2$, $Y^3$, and $Y^4$ have the same definitions as X, m, $G^1$, $Y^1$, $Y^2$, $Y^3$, and $Y^4$ in Formula (5) above, respectively.

The compound represented by Formula (7) is produced using, for example, 2-aminobenzotrifluoride and a benzoic acid derivative, as the raw materials. The benzoic acid derivative can be produced by the method described in WO 2010/18857, using 2-chloro-3-nitrobenzoic acid as the raw material.

$Z^1$ in Formula (3) represents a C1-C6 alkyl group or a C1-C6 haloalkyl group. $Z^1$ is preferably a C1-C6 haloalkyl group, and more preferably a C1-C6 perfluoroalkyl group.

Xa represents an iodine atom or a bromine atom.

n2 in Formula (4) represents an integer from 1 to 4, and preferably an integer from 1 to 3.

$Z^1$ has the same definition as $Z^1$ in Formula (3) above, and so are the preferable examples.

X, m, $G^1$, Y, and A have the same definitions as X, m, $G^1$, Y, and A in Formula (1) above, respectively, and so are the preferable examples.

The alkylated aromatic amide derivative represented by Formula (4) above is preferably an alkylated aromatic amide derivative represented by the following Formula (6), and more preferably an alkylated aromatic amide derivative represented by the following Formula (8).

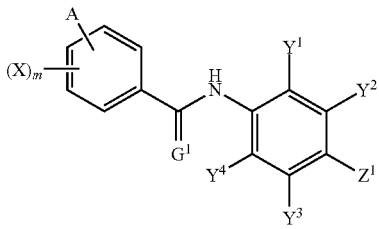

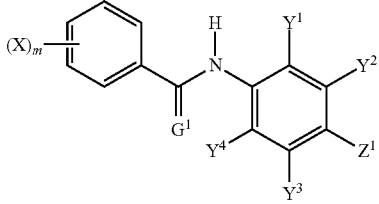

$Z^1$ in Formula (6) has the same definition as $Z^1$ in Formula (3) above, and so are the preferable examples. $Y^1$, $Y^2$, $Y^3$, $Y^4$, X, m, $G^1$, and A have the same definitions as $Y^1$, $Y^2$, $Y^3$, $Y^4$, X, m, $G^1$, and A in Formula (5) above, respectively, and so are the preferable examples.

$Z^1$ in Formula (8) has the same definition as $Z^1$ in Formula (3) above, and so are the preferable examples. $Y^1$, $Y^2$, $Y^3$, $Y^4$, X, m, $G^1$, $G^2$, $Q^1$, and $R^1$ have the same definitions as $Y^1$, $Y^2$, $Y^3$, $Y^4$, X, m, $G^1$, $G^2$, $Q^1$, and $R^1$ in Formula (7) above, respectively, and so are the preferable examples.

Examples of the metal to be used in the reaction between the aromatic amide derivative represented by Formula (1) and the haloalkyl compound represented by Formula (3) may include lithium, sodium, calcium, magnesium, zinc, aluminium, manganese, tungsten, tin, chromium, gold, platinum, silver, copper, iron, nickel, cobalt, lead, titanium, and any alloys thereof. Among them, at least one selected from the group consisting of copper, iron, and zinc is preferable.

Examples of the metal salt to be used in the above reaction may include iron metal salts showing a valency of two, specific examples thereof including ammonium iron(II) sulfate, iron(II) fluoride, iron(II) chloride, iron(II) bromide, iron(II) iodide, iron(II) sulfate, iron(II) oxalate, potassium hexacyanoferrate(II), iron(II) gluconate n-hydrate, tris(1,10-phenanthroline) iron(II) sulfate, ammonium iron(III) hexacyanoferrate(II), iron(II) stearate, ammonium hexacyanoferrate (II), iron(II) fumarate, iron(II) acetate, iron(II) naphthenate, iron(II) tetrafluoroborate, iron(II) amidosulfate, iron(II) titanium oxide, and iron(II) ethylenediammonium sulfate; copper metals showing a valency of one, specific examples thereof including copper(I) chloride, copper(I) cyanide, copper(I) bromide, copper(I) iodide, copper(I) sulfide, copper(I)

acetate, copper(I) trifluoromethanethiol, and copper(I) thiocyanate; and samarium(II) iodide. Above all, iron(II) chloride, iron(II) sulfate, and iron(II) sulfate hydrate are preferable.

The metals and metal ions described above may be used singly or in mixture of two or more kinds thereof. The amount thereof to be used is not particularly limited, but usually, the metal or metal ion may be used in an amount appropriately selected within the range of from 0.01-fold molar equivalents to 5-fold molar equivalents, and preferably within the range of from 1-fold molar equivalent to 2-fold molar equivalents, with respect to the aromatic amide derivative represented by Formula (1), which is the reaction raw material.

Examples of the base to be used in the above reaction may include organic bases such as triethylamine, tri-n-butylamine, pyridine, and 4-dimethylaminopyridine; alkali metal hydroxides such as sodium hydroxide and potassium hydroxide; carbonates such as sodium hydrogencarbonate and potassium carbonate; phosphates such as dipotassium monohydrogen phosphate and trisodium phosphate; hydrogenated alkali metal salts such as sodium hydride; and alkali metal alcoholates such as sodium methoxide and sodium ethoxide.

Among them, alkali metal hydroxides such as sodium hydroxide or potassium hydroxide can be particularly preferably used.

Such base may be used in an amount appropriately selected within the range of from 0.01-fold molar equivalents to 10-fold molar equivalents, and preferably within the range of from 5-fold molar equivalents to 10-fold molar equivalents, with respect to the aromatic amide derivative represented by Formula (1).

The above reaction may be carried out in the absence of a solvent or may be carried out in the presence of an inert solvent.

In the case of carrying out the reaction in the presence of an inert solvent, the inert solvent is not particularly limited as long as the solvent does not significantly inhibit the progress of the reaction. Examples of the inert solvent may include water; aromatic hydrocarbons such as benzene, toluene, and xylene; halogenated hydrocarbons such as dichloromethane, chloroform, and tetrachlorocarbon; chained or cyclic ethers such as diethyl ether, dioxane, tetrahydrofuran, and 1,2-dimethoxyethane; esters such as ethyl acetate and butyl acetate; alcohols such as methanol and ethanol; ketones such as acetone, methyl isobutyl ketone, and cyclohexanone; amides such as N,N-dimethylformamide, N,N-dimethylacetamide, 1,3-dimethyl-2-imidazolidinone, and N-methyl-2-pyrrolidone; nitriles such as acetonitrile; and dimethylsulfoxide. These solvents may be used singly or in mixture of two or more kinds thereof.

Among them, amides such as N,N-dimethylformamide, N,N-dimethylacetamide, 1,3-dimethyl-2-imidazolidinone, or N-methyl-2-pyrrolidone, and dimethylsulfoxide can be particularly preferably used.

Concerning the amount of the inert solvent used, such inert solvent may be used in an amount appropriately selected within the range of from 2-fold by weight to 20-fold by weight, and preferably within the range of from 5-fold by weight to 15-fold by weight, with respect to the aromatic amide derivative represented by Formula (1).

The reaction temperature in the above reaction may be appropriately selected within the range of from −20° C. to 200° C., and in the case of using an inert solvent, the reaction temperature may be any temperature that is lower than or equal to the boiling point. The reaction time may be appropriately selected within the range of from several minutes to 96 hours.

The mixing ratio of the haloalkyl compound represented by Formula (3) relative to the aromatic amide derivative represented by Formula (1) in the above reaction is not particularly limited. From the economic point of view, it is preferable that the mixing ratio is from 1-fold molar equivalent to 3-fold molar equivalents.

In the production method as described in the above, the alkylated aromatic amide derivative represented by Formula (4), which is the aimed product, may be isolated from the reaction system after the completion of the reaction, according to a conventional method and, if necessary, purification may be carried out by an operation such as recrystallization, column chromatography, or distillation.

The method for producing a halogenated aromatic amide derivative represented by Formula (10) according to the invention includes a first process of allowing an aromatic amide derivative represented by the following Formula (7a) and a haloalkyl compound represented by the following Formula (3) to reach with each other in the presence of a base and a metal or metal salt, to obtain an alkylated aromatic amide derivative represented by the following Formula (9), and a second process of halogenating the alkylated aromatic amide derivative represented by Formula (9) under a basic condition. The production method above may further include other process(es), if necessary.

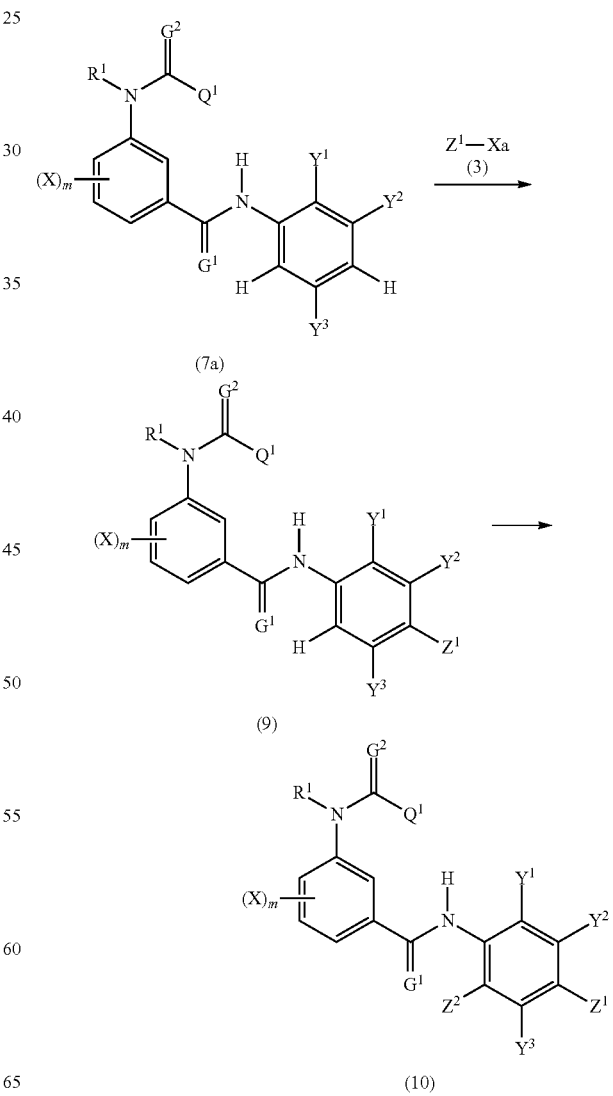

$G^2$, $Q^1$, and $R^1$ in Formula (7a) have the same definitions as $G^2$, $Q^1$, and $R^1$ in Formula (2) above, respectively. X, m, $G^1$, $Y^1$, $Y^2$, and $Y^3$ have the same definitions as X, m, $G^1$, $Y^1$, $Y^2$, and $Y^3$ in Formula (5) above, respectively.

$Z^1$ in Formula (9) has the same definition as $Z^1$ in Formula (3). X, m, $G^1$, $G^2$, $Q^1$, $R^1$, $Y^1$, $Y^2$, and $Y^3$ have the same definitions as X, m, $G^1$, $G^2$, $Q^1$, $R^1$, $Y^1$, $Y^2$, and $Y^3$ in Formula (7a) above, respectively.

The details of the first process are the same as those of the above-described method for producing an alkylated aromatic amide derivative represented by Formula (4).

In the second process, the alkylated aromatic amide derivative represented by Formula (9) is halogenated under a basic conditions, thereby producing a halogenated aromatic amide derivative represented by Formula (10). The second process can be carried out, for example, using the alkylated aromatic amide derivative represented by Formula (9) and a halogenating agent under a basic condition, in an inert solvent or in the absence of a solvent.

The halogenating agent is not particularly limited as long as the substance can replace a hydrogen atom with a chlorine atom, a bromine atom, or a iodine atom. Specific examples of the halogenating agent may include chlorine, bromine, iodine, sulfuryl chloride, N-chlorosuccinimide, N-bromosuccinimide, N-iodosuccinimide, iodine monochloride, 1,3-dibromo-5,5-dimethylhydantoin, and 1,3-diiodo-5,5-dimethylhydantoin.

The amount of the halogenating agent used in the above reaction is preferably from 1.0-fold molar equivalents to 5-fold molar equivalents, and more preferably from 1.01-fold molar equivalents to 1.5-fold molar equivalents, with respect to the alkylated aromatic amide derivative represented by Formula (9).

The inert solvent, which is used in the above reaction, is not particularly limited as long as the solvent does not significantly inhibit the progress of the reaction. Examples of the inert solvent may include water; aromatic hydrocarbons such as benzene, toluene, and xylene; halogenated hydrocarbons such as dichloromethane, chloroform, and tetrachlorocarbon; chained or cyclic ethers such as diethyl ether, dioxane, tetrahydrofuran, and 1,2-dimethoxyethane; esters such as ethyl acetate and butyl acetate; alcohols such as methanol and ethanol; ketones such as acetone, methyl isobutyl ketone, and cyclohexanone; amides such as N,N-dimethylformamide, N,N-dimethylacetamide, 1,3-dimethyl-2-imidazolidinone, and N-methyl-2-pyrrolidone; nitriles such as acetonitrile; and dimethylsulfoxide. These solvents may be used singly or in mixture of two or more kinds thereof.

Among them, amides such as N,N-dimethylformamide, N,N-dimethylacetamide, 1,3-dimethyl-2-imidazolidinone, or N-methyl-2-pyrrolidone; and dimethylsulfoxide can be particularly preferably used.

The amount of the inert solvent used may be in an amount appropriately selected within the range of from 2-fold by weight to 10-fold by weight, and preferably within the range of from 3-fold by weight to 8-fold by weight, with respect to the alkylated aromatic amide derivative represented by Formula (9).

Examples of the base to be used in the above reaction may include organic bases such as triethylamine, tri-n-butylamine, pyridine, and 4-dimethylaminopyridine; alkali metal hydroxides such as sodium hydroxide and potassium hydroxide; carbonates such as sodium hydrogencarbonate and potassium carbonate; phosphates such as dipotassium monohydrogen phosphate and trisodium phosphate; hydrogenated alkali metal salts such as sodium hydride; and alkali metal alcoholates such as sodium methoxide and sodium ethoxide.

Among them, hydrogenated alkali metal salts such as sodium hydride, and alkali metal hydroxides such as sodium hydroxide can be particularly preferably used.

Such base may be used in an amount appropriately selected within the range of from 0.01-fold molar equivalents to 5-fold molar equivalents, and preferably within the range of from 1-fold molar equivalent to 3-fold molar equivalents, with respect to the aromatic amide derivative represented by Formula (9).

The reaction temperature may be appropriately selected, for example, within the range of from −20° C. to 200° C. and in the case of using an inert solvent, the reaction temperature may be any temperature that is lower than or equal to the boiling point. The reaction time may be appropriately selected within the range of from several minutes to 96 hours.

In the production method as described in the above, the aimed product may be isolated from the reaction system after the completion of the reaction, according to a conventional method. If necessary, purification may be carried out by an operation such as recrystallization, column chromatography, or distillation.

Hereinafter, the representative compounds among the compounds represented by Formula (7), which are the effective intermediates according to the invention, are shown in Table 1 to Table 3, but the invention is not limited thereto.

In the tables, "Me" represents a methyl group, "Et" represents an ethyl group, "H" represents a hydrogen atom, "F" represents a fluorine atom, "Cl" represents a chlorine atom, "Br" represents a bromine atom, "I" represents an iodine atom, and "CF3" represents a trifluoromethyl group.

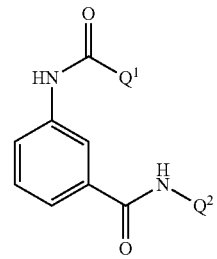

TABLE I

| Compound No. | $Q_1$ | $Q_2$ |
|---|---|---|
| 1 | phenyl | 2,6-dichlorophenyl |
| 2 | 2-fluorophenyl | 2,6-dibromophenyl |
| 3 | 4-fluorophenyl | 2,6-dibromophenyl |
| 4 | 4-nitrophenyl | 2,6-dibromophenyl |
| 5 | 4-cyanophenyl | 2,6-dibromophenyl |
| 6 | 2-chloropyridin-3-yl | 2,6-dibromophenyl |
| 7 | phenyl | 2,6-dimethylphenyl |
| 8 | 2-fluorophenyl | 2,6-dimethylphenyl |

TABLE I-continued

| Compound No. | Q₁ | Q₂ |
|---|---|---|
| 9 | 4-fluorophenyl | 2,6-dimethylphenyl |
| 10 | 4-nitrophenyl | 2,6-dimethylphenyl |
| 11 | 4-cyanophenyl | 2,6-dimethylphenyl |
| 12 | 2-chloropyridin-3-yl | 2,6-dimethylphenyl |
| 13 | phenyl | 2-bromo-6-methylphenyl |
| 14 | phenyl | 2-ethyl-6-methylphenyl |
| 15 | 4-fluorophenyl | 2-ethyl-6-methylphenyl |
| 16 | phenyl | 2-iodo-6-methylphenyl |
| 17 | phenyl | 2-hydroxy-6-methylphenyl |
| 18 | phenyl | 2-chloro-6-ethylphenyl |
| 19 | phenyl | 2-bromo-6-ethylphenyl |
| 20 | 4-fluorophenyl | 2-bromo-6-ethylphenyl |
| 21 | phenyl | 2-ethyl-6-iodophenyl |
| 22 | 4-fluorophenyl | 2-ethyl-6-iodophenyl |
| 23 | 4-nitrophenyl | 2-ethyl-6-iodophenyl |
| 24 | 4-cyanophenyl | 2-ethyl-6-iodophenyl |
| 25 | 4-nitrophenyl | 2-methyl-6-n-propylphenyl |
| 26 | phenyl | 2-isopropyl-6-methylphenyl |
| 27 | 4-fluorophenyl | 2-isopropyl-6-methylphenyl |
| 28 | phenyl | 2-bromo-6-n-propylphenyl |
| 29 | 4-fluorophenyl | 2-bromo-6-n-propylphenyl |
| 30 | 4-nitrophenyl | 2-bromo-6-n-propylphenyl |
| 31 | 4-cyanophenyl | 2-bromo-6-n-propylphenyl |
| 32 | phenyl | 2-iodo-6-n-propylphenyl |
| 33 | 4-fluorophenyl | 2-iodo-6-n-propylphenyl |
| 34 | 4-nitrophenyl | 2-iodo-6-n-propylphenyl |
| 35 | 4-cyanophenyl | 2-iodo-6-n-propylphenyl |
| 36 | 4-trifluoromethylphenyl | 2-iodo-6-n-propylphenyl |
| 37 | phenyl | 2-chloro-6-n-butylphenyl |
| 38 | 4-fluorophenyl | 2-chloro-6-n-butylphenyl |
| 39 | phenyl | 2-bromo-6-n-butylphenyl |
| 40 | 4-fluorophenyl | 2-bromo-6-n-butylphenyl |
| 41 | phenyl | 2-iodo-6-n-butylphenyl |
| 42 | 4-fluorophenyl | 2-iodo-6-n-butylphenyl |
| 43 | phenyl | 2-(2-butyl)-6-chlorophenyl |
| 44 | phenyl | 2-bromo-6-(2-butyl)phenyl |
| 45 | 4-fluorophenyl | 2-bromo-6-(2-butyl)phenyl |
| 46 | phenyl | 2-(2-butyl)-6-iodophenyl |
| 47 | 4-fluorophenyl | 2-bromo-6-cyanophnyl |
| 48 | phenyl | 2-bromo-6-methylthiophenyl |
| 49 | 4-fluorophenyl | 2-bromo-6-methylthiophenyl |
| 50 | phenyl | 2-bromo-6-(methylsulfinyl)phenyl |
| 51 | 4-fluorophenyl | 2-chloro-6-(methylsulfonyl)phenyl |
| 52 | 2-chloropyridin-3-yl | 2-chloro-6-(methylsulfonyl)phenyl |
| 53 | phenyl | 2-bromo-6-(methylsulfonyl)phenyl |
| 54 | 4-fluorophenyl | 2-bromo-6-(methylsulfonyl)phenyl |
| 55 | 4-fluorophenyl | 2-bromo-6-(methylsulfonyl)phenyl |
| 56 | 4-nitrophenyl | 2-bromo-6-(methylsulfonyl)phenyl |
| 57 | 4-cyanophenyl | 2-bromo-6-(methylsulfonyl)phenyl |
| 58 | 2-chloropyridin-3-yl | 2-bromo-6-(methylsulfonyl)phenyl |
| 59 | phenyl | 2-methylthiomethyl-6-trifluoromethylphenyl |
| 60 | phenyl | 2-bromo-6-(trifluoromethylthio)phenyl |
| 61 | phenyl | 2-trifluoromethylphenyl |
| 62 | 2-fluorophenyl | 2-trifluoromethylphenyl |
| 63 | 4-fluorophenyl | 2-trifluoromethylphenyl |
| 64 | 4-nitrophenyl | 2-trifluoromethylphenyl |
| 65 | 4-cyanophenyl | 2-trifluoromethylphenyl |
| 66 | 2-chloropyridin-3-yl | 2-trifluoromethylphenyl |
| 67 | phenyl | 2-pentafluoroethylphenyl |
| 68 | 2-fluorophenyl | 2-pentafluoroethylphenyl |
| 69 | 4-fluorophenyl | 2-pentafluoroethylphenyl |
| 70 | 4-nitrophenyl | 2-pentafluoroethylphenyl |
| 71 | 4-cyanophenyl | 2-pentafluoroethylphenyl |
| 72 | 2-chloropyridin-3-yl | 2-pentafluoroethylphenyl |
| 73 | phenyl | 2-methylphenyl |
| 74 | 2-fluorophenyl | 2-methylphenyl |
| 75 | 4-fluorophenyl | 2-methylphenyl |
| 76 | 4-nitrophenyl | 2-methylphenyl |
| 77 | 4-cyanophenyl | 2-methylphenyl |
| 78 | 2-chloropyridin-3-yl | 2-methylphenyl |
| 79 | phenyl | 2-fluorophenyl |
| 80 | 2-fluorophenyl | 2-fluorophenyl |
| 81 | 4-fluorophenyl | 2-fluorophenyl |
| 82 | 4-nitrophenyl | 2-fluorophenyl |
| 83 | 4-cyanophenyl | 2-fluorophenyl |
| 84 | 2-chloropyridin-3-yl | 2-fluorophenyl |
| 85 | phenyl | 2-chlorophenyl |
| 86 | 2-fluorophenyl | 2-chlorophenyl |

TABLE 1-continued

| Compound No. | $Q_1$ | $Q_2$ |
|---|---|---|
| 87 | 4-fluorophenyl | 2-chlorophenyl |
| 88 | 4-nitrophenyl | 2-chlorophenyl |
| 89 | 4-cyanophenyl | 2-chlorophenyl |
| 90 | 2-chloropyridin-3-yl | 2-chlorophenyl |
| 91 | phenyl | 2-bromophenyl |
| 92 | 2-fluorophenyl | 2-bromophenyl |
| 93 | 4-fluorophenyl | 2-bromophenyl |
| 94 | 4-nitrophenyl | 2-bromophenyl |
| 95 | 4-cyanophenyl | 2-bromophenyl |
| 96 | 2-chloropyridin-3-yl | 2-bromophenyl |
| 97 | phenyl | 2-iodophenyl |
| 98 | 2-fluorophenyl | 2-iodophenyl |
| 99 | 4-fluorophenyl | 2-iodophenyl |
| 100 | 4-nitrophenyl | 2-iodophenyl |
| 101 | 4-cyanophenyl | 2-iodophenyl |
| 102 | 2-chloropyridin-3-yl | 2-iodophenyl |
| 103 | phenyl | 2-iodophenyl |
| 104 | 2-fluorophenyl | 2-iodophenyl |
| 105 | 4-fluorophenyl | 2-iodophenyl |
| 106 | 4-nitrophenyl | 2-iodophenyl |
| 107 | 4-cyanophenyl | 2-iodophenyl |
| 108 | 2-chloropyridin-3-yl | 2-iodophenyl |
| 109 | phenyl | 2-trifluoromethylthiophenyl |
| 110 | 2-fluorophenyl | 2-trifluoromethylthiophenyl |
| 111 | 4-fluorophenyl | 2-trifluoromethylthiophenyl |
| 112 | 4-nitrophenyl | 2-trifluoromethylthiophenyl |
| 113 | 4-cyanophenyl | 2-trifluoromethylthiophenyl |
| 114 | 2-chloropyridin-3-yl | 2-trifluoromethylthiophenyl |

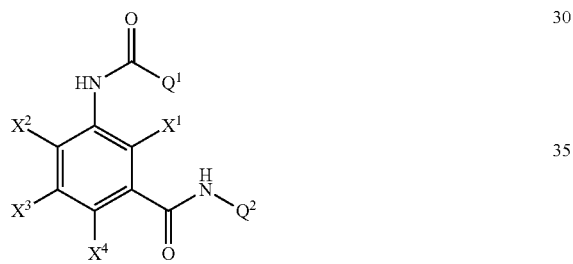

TABLE 2

| Compound No. | $Q^1$ | $X^1$ | $X^2$ | $X^3$ | $X^4$ | $Q^2$ |
|---|---|---|---|---|---|---|
| 115 | phenyl | F | H | H | H | 2,6-dimethylphenyl |
| 116 | 2-fluorophenyl | F | H | H | H | 2,6-dimethylphenyl |
| 117 | 4-fluorophenyl | F | H | H | H | 2,6-dimethylphenyl |
| 118 | 4-nitrophenyl | F | H | H | H | 2,6-dimethylphenyl |
| 119 | 4-cyanophenyl | F | H | H | H | 2,6-dimethylphenyl |
| 120 | 2-chloropyridin-3-yl | F | H | H | H | 2,6-dimethylphenyl |
| 121 | phenyl | H | Cl | H | H | 2,6-dimethylphenyl |
| 122 | phenyl | H | F | H | H | 2,6-dimethylphenyl |
| 123 | 4-nitrophenyl | H | F | H | H | 2,6-dimethylphenyl |
| 124 | 4-cyanophenyl | H | F | H | H | 2,6-dimethylphenyl |
| 125 | 2-fluorophenyl | H | F | H | H | 2,6-dimethylphenyl |
| 126 | 4-fluorophenyl | H | F | H | H | 2,6-dimethylphenyl |
| 127 | 4-trifluoromethylphenyl | H | F | H | H | 2,6-dimethylphenyl |
| 128 | 2,4-difluorophenyl | H | F | H | H | 2,6-dimethylphenyl |
| 129 | 2-chloropyridin-3-yl | H | F | H | H | 2,6-dimethylphenyl |
| 130 | phenyl | H | H | CF3 | H | 2,6-dimethylphenyl |
| 131 | phenyl | H | H | H | F | 2,6-dimethylphenyl |
| 132 | phenyl | H | H | H | Cl | 2,6-dimethylphenyl |
| 133 | phenyl | H | H | H | Br | 2,6-dimethylphenyl |
| 134 | phenyl | H | H | H | I | 2,6-dimethylphenyl |
| 135 | phenyl | F | H | H | F | 2,6-dimethylphenyl |
| 136 | phenyl | H | Br | H | Br | 2,6-dimethylphenyl |
| 137 | phenyl | F | H | H | H | 2-trifluoromethylphenyl |
| 138 | 2-fluorophenyl | F | H | H | H | 2-trifluoromethylphenyl |
| 139 | 4-fluorophenyl | F | H | H | H | 2-trifluoromethylphenyl |

TABLE 2-continued

| Compound No. | Q¹ | X¹ | X² | X³ | X⁴ | Q² |
|---|---|---|---|---|---|---|
| 140 | 4-nitrophenyl | F | H | H | H | 2-trifluoromethylphenyl |
| 141 | 4-cyanophenyl | F | H | H | H | 2-trifluoromethylphenyl |
| 142 | 2-chloropyridin-3-yl | F | H | H | H | 2-trifluoromethylphenyl |
| 143 | phenyl | F | H | H | H | 2-pentafluoroethylphenyl |
| 144 | 2-fluorophenyl | F | H | H | H | 2-pentafluoroethylphenyl |
| 145 | 4-fluorophenyl | F | H | H | H | 2-pentafluoroethylphenyl |
| 146 | 4-nitrophenyl | F | H | H | H | 2-pentafluoroethylphenyl |
| 147 | 4-cyanophenyl | F | H | H | H | 2-pentafluoroethylphenyl |
| 148 | 2-chloropyridin-3-yl | F | H | H | H | 2-pentafluoroethylphenyl |
| 149 | phenyl | F | H | H | H | 2-methylphenyl |
| 150 | 2-fluorophenyl | F | H | H | H | 2-methylphenyl |
| 151 | 4-fluorophenyl | F | H | H | H | 2-methylphenyl |
| 152 | 4-nitrophenyl | F | H | H | H | 2-methylphenyl |
| 153 | 4-cyanophenyl | F | H | H | H | 2-methylphenyl |
| 154 | 2-chloropyridin-3-yl | F | H | H | H | 2-methylphenyl |
| 155 | phenyl | F | H | H | H | 2-fluorophenyl |
| 156 | 2-fluorophenyl | F | H | H | H | 2-fluorophenyl |
| 157 | 4-fluorophenyl | F | H | H | H | 2-fluorophenyl |
| 158 | 4-nitrophenyl | F | H | H | H | 2-fluorophenyl |
| 159 | 4-cyanophenyl | F | H | H | H | 2-fluorophenyl |
| 160 | 2-chloropyridin-3-yl | F | H | H | H | 2-fluorophenyl |
| 161 | phenyl | F | H | H | H | 2-chlorophenyl |
| 162 | 2-fluorophenyl | F | H | H | H | 2-chlorophenyl |
| 163 | 4-fluorophenyl | F | H | H | H | 2-chlorophenyl |
| 164 | 4-nitrophenyl | F | H | H | H | 2-chlorophenyl |
| 165 | 4-cyanophenyl | F | H | H | H | 2-chlorophenyl |
| 166 | 2-chloropyridin-3-yl | F | H | H | H | 2-chlorophenyl |
| 167 | phenyl | F | H | H | H | 2-bromophenyl |
| 168 | 2-fluorophenyl | F | H | H | H | 2-bromophenyl |
| 169 | 4-fluorophenyl | F | H | H | H | 2-bromophenyl |
| 170 | 4-nitrophenyl | F | H | H | H | 2-bromophenyl |
| 171 | 4-cyanophenyl | F | H | H | H | 2-bromophenyl |
| 172 | 2-chloropyridin-3-yl | F | H | H | H | 2-bromophenyl |
| 173 | phenyl | F | H | H | H | 2-iodophenyl |
| 174 | 2-fluorophenyl | F | H | H | H | 2-iodophenyl |
| 175 | 4-fluorophenyl | F | H | H | H | 2-iodophenyl |
| 176 | 4-nitrophenyl | F | H | H | H | 2-iodophenyl |
| 177 | 4-cyanophenyl | F | H | H | H | 2-iodophenyl |
| 178 | 2-chloropyridin-3-yl | F | H | H | H | 2-iodophenyl |
| 179 | phenyl | F | H | H | H | 2-iodophenyl |
| 180 | 2-fluorophenyl | F | H | H | H | 2-iodophenyl |
| 181 | 4-fluorophenyl | F | H | H | H | 2-iodophenyl |
| 182 | 4-nitrophenyl | F | H | H | H | 2-iodophenyl |
| 183 | 4-cyanophenyl | F | H | H | H | 2-iodophenyl |
| 184 | 2-chloropyridin-3-yl | F | H | H | H | 2-iodophenyl |
| 185 | phenyl | F | H | H | H | 2-trifluoromethylthiophenyl |
| 186 | 2-fluorophenyl | F | H | H | H | 2-trifluoromethylthiophenyl |
| 187 | 4-fluorophenyl | F | H | H | H | 2-trifluoromethylthiophenyl |
| 188 | 4-nitrophenyl | F | H | H | H | 2-trifluoromethylthiophenyl |
| 189 | 4-cyanophenyl | F | H | H | H | 2-trifluoromethylthiophenyl |
| 190 | 2-chloropyridin-3-yl | F | H | H | H | 2-trifluoromethylthiophenyl |

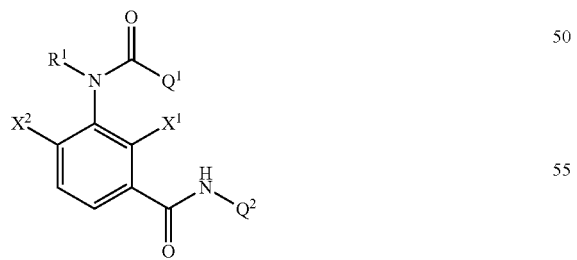

TABLE 3

| Compound No. | Q¹ | R¹ | X¹ | X² | Q² |
|---|---|---|---|---|---|
| 191 | phenyl | Me | H | H | 2,6-dimethylphenyl |
| 192 | 2-methylphenyl | Me | H | H | 2,6-dimethylphenyl |

TABLE 3-continued

| Compound No. | Q¹ | R¹ | X¹ | X² | Q² |
|---|---|---|---|---|---|
| 193 | 4-methylphenyl | Me | H | H | 2,6-dimethylphenyl |
| 194 | 2-fluorophenyl | Me | H | H | 2,6-dimethylphenyl |
| 195 | 3-fluorophenyl | Me | H | H | 2,6-dimethylphenyl |
| 196 | 4-fluorophenyl | Me | H | H | 2,6-dimethylphenyl |
| 197 | 2-chlorophenyl | Me | H | H | 2,6-dimethylphenyl |
| 198 | 4-chlorophenyl | Me | H | H | 2,6-dimethylphenyl |
| 199 | 2-bromophenyl | Me | H | H | 2,6-dimethylphenyl |
| 200 | 2-iodophenyl | Me | H | H | 2,6-dimethylphenyl |
| 201 | 3-cyanophenyl | Me | H | H | 2,6-dimethylphenyl |
| 202 | 4-cyanophenyl | Me | H | H | 2,6-dimethylphenyl |
| 203 | 2-nitrophenyl | Me | H | H | 2,6-dimethylphenyl |
| 204 | 3-nitrophenyl | Me | H | H | 2,6-dimethylphenyl |
| 205 | 4-nitrophenyl | Me | H | H | 2,6-dimethylphenyl |
| 206 | 2-trifluoromethylphenyl | Me | H | H | 2,6-dimethylphenyl |
| 207 | 4-trifluoromethylphenyl | Me | H | H | 2,6-dimethylphenyl |
| 208 | 4-trifluoromethoxyphenyl | Me | H | H | 2,6-dimethylphenyl |
| 209 | 2,3-difluorophenyl | Me | H | H | 2,6-dimethylphenyl |
| 210 | 2,4-difluorophenyl | Me | H | H | 2,6-dimethylphenyl |
| 211 | 2,5-difluorophenyl | Me | H | H | 2,6-dimethylphenyl |
| 212 | 2,6-difluorophenyl | Me | H | H | 2,6-dimethylphenyl |
| 213 | 2,4-dichlorophenyl | Me | H | H | 2,6-dimethylphenyl |
| 214 | 2,6-dichlorophenyl | Me | H | H | 2,6-dimethylphenyl |
| 215 | 3,4-dichlorophenyl | Me | H | H | 2,6-dimethylphenyl |
| 216 | 2-chloro-4-nitrophenyl | Me | H | H | 2,6-dimethylphenyl |
| 217 | 2-chloro-4-fluorophenyl | Me | H | H | 2,6-dimethylphenyl |
| 218 | 2-chloro-6-fluorophenyl | Me | H | H | 2,6-dimethylphenyl |
| 219 | 4-chloro-2-fluorophenyl | Me | H | H | 2,6-dimethylphenyl |
| 220 | 4-chloro-2-nitrophenyl | Me | H | H | 2,6-dimethylphenyl |
| 221 | 2,3,6-trifluorophenyl | Me | H | H | 2,6-dimethylphenyl |
| 222 | 3-(acetylamino)phenyl | Me | H | H | 2,6-dimethylphenyl |
| 223 | pyridin-2-yl | Me | H | H | 2,6-dimethylphenyl |
| 224 | pyridin-3-yl | Me | H | H | 2,6-dimethylphenyl |
| 225 | 2-fluoropyridin-3-yl | Me | H | H | 2,6-dimethylphenyl |
| 226 | 2-chloropyridin-3-yl | Me | H | H | 2,6-dimethylphenyl |
| 227 | 2-chloropyridin-5-yl | Me | H | H | 2,6-dimethylphenyl |
| 228 | 2-trifluoromethylpyridin-3-yl | Me | H | H | 2,6-dimethylphenyl |
| 229 | 2-methylthiopyridin-3-yl | Me | H | H | 2,6-dimethylphenyl |
| 230 | pyrazin-2-yl | Me | H | H | 2,6-dimethylphenyl |
| 231 | furan-2-yl | Me | H | H | 2,6-dimethylphenyl |
| 232 | furan-3-yl | Me | H | H | 2,6-dimethylphenyl |
| 233 | 2-tetrahydrofuranyl | Me | H | H | 2,6-dimethylphenyl |
| 234 | benzofuran-2-yl | Me | H | H | 2,6-dimethylphenyl |
| 235 | thiophen-2-yl | Me | H | H | 2,6-dimethylphenyl |
| 236 | phenyl | Me | H | H | 2-bromo-6-(methylsulfonyl)phenyl |
| 237 | 2-methylphenyl | Me | H | H | 2-bromo-6-(methylsulfonyl)phenyl |
| 238 | 4-methylphenyl | Me | H | H | 2-bromo-6-(methylsulfonyl)phenyl |
| 239 | 2-fluorophenyl | Me | H | H | 2-bromo-6-(methylsulfonyl)phenyl |
| 240 | 3-fluorophenyl | Me | H | H | 2-bromo-6-(methylsulfonyl)phenyl |
| 241 | 4-fluorophenyl | Me | H | H | 2-bromo-6-(methylsulfonyl)phenyl |
| 242 | 2-chlorophenyl | Me | H | H | 2-bromo-6-(methylsulfonyl)phenyl |
| 243 | 4-chlorophenyl | Me | H | H | 2-bromo-6-(methylsulfonyl)phenyl |
| 244 | 2-bromophenyl | Me | H | H | 2-bromo-6-(methylsulfonyl)phenyl |
| 245 | 2-iodophenyl | Me | H | H | 2-bromo-6-(methylsulfonyl)phenyl |
| 246 | 3-cyanophenyl | Me | H | H | 2-bromo-6-(methylsulfonyl)phenyl |
| 247 | 4-cyanophenyl | Me | H | H | 2-bromo-6-(methylsulfonyl)phenyl |
| 248 | 2-nitrophenyl | Me | H | H | 2-bromo-6-(methylsulfonyl)phenyl |
| 249 | 3-nitrophenyl | Me | H | H | 2-bromo-6-(methylsulfonyl)phenyl |
| 250 | 4-nitrophenyl | Me | H | H | 2-bromo-6-(methylsulfonyl)phenyl |
| 251 | 2-trifluoromethylphenyl | Me | H | H | 2-bromo-6-(methylsulfonyl)phenyl |
| 252 | 4-trifluoromethylphenyl | Me | H | H | 2-bromo-6-(methylsulfonyl)phenyl |

TABLE 3-continued

| Compound No. | Q¹ | R¹ | X¹ | X² | Q² |
|---|---|---|---|---|---|
| 253 | 4-trifluoromethoxyphenyl | Me | H | H | 2-bromo-6-(methylsulfonyl)phenyl |
| 254 | 2,3-difluorophenyl | Me | H | H | 2-bromo-6-(methylsulfonyl)phenyl |
| 255 | 2,4-difluorophenyl | Me | H | H | 2-bromo-6-(methylsulfonyl)phenyl |
| 256 | 2,5-difluorophenyl | Me | H | H | 2-bromo-6-(methylsulfonyl)phenyl |
| 257 | 2,6-difluorophenyl | Me | H | H | 2-bromo-6-(methylsulfonyl)phenyl |
| 258 | 2,4-dichlorophenyl | Me | H | H | 2-bromo-6-(methylsulfonyl)phenyl |
| 259 | 2,6-dichlorophenyl | Me | H | H | 2-bromo-6-(methylsulfonyl)phenyl |
| 260 | 3,4-dichlorophenyl | Me | H | H | 2-bromo-6-(methylsulfonyl)phenyl |
| 261 | 2-chloro-4-nitrophenyl | Me | H | H | 2-bromo-6-(methylsulfonyl)phenyl |
| 262 | 2-chloro-4-fluorophenyl | Me | H | H | 2-bromo-6-(methylsulfonyl)phenyl |
| 263 | 2-chloro-6-fluorophenyl | Me | H | H | 2-bromo-6-(methylsulfonyl)phenyl |
| 264 | 4-chloro-2-fluorophenyl | Me | H | H | 2-bromo-6-(methylsulfonyl)phenyl |
| 265 | 4-chloro-2-nitrophenyl | Me | H | H | 2-bromo-6-(methylsulfonyl)phenyl |
| 266 | 2,3,6-trifluorophenyl | Me | H | H | 2-bromo-6-(methylsulfonyl)phenyl |
| 267 | pyridin-2-yl | Me | H | H | 2-bromo-6-(methylsulfonyl)phenyl |
| 268 | pyridin-3-yl | Me | H | H | 2-bromo-6-(methylsulfonyl)phenyl |
| 269 | 2-fluoropyridin-3-yl | Me | H | H | 2-bromo-6-(methylsulfonyl)phenyl |
| 270 | 2-chloropyridin-3-yl | Me | H | H | 2-bromo-6-(methylsulfonyl)phenyl |
| 271 | 2-chloropyridin-5-yl | Me | H | H | 2-bromo-6-(methylsulfonyl)phenyl |
| 272 | 2-methylthiopyridin-3-yl | Me | H | H | 2-bromo-6-(methylsulfonyl)phenyl |
| 273 | pyrazin-2-yl | Me | H | H | 2-bromo-6-(methylsulfonyl)phenyl |
| 274 | furan-2-yl | Me | H | H | 2-bromo-6-(methylsulfonyl)phenyl |
| 275 | thiophen-2-yl | Me | H | H | 2-bromo-6-(methylsulfonyl)phenyl |
| 276 | phenyl | Me | H | H | 2-n-propyl-6-iodophenyl |
| 277 | 2-methylphenyl | Me | H | H | 2-n-propyl-6-iodophenyl |
| 278 | 4-methylphenyl | Me | H | H | 2-n-propyl-6-iodophenyl |
| 279 | 2-fluorophenyl | Me | H | H | 2-n-propyl-6-iodophenyl |
| 280 | 3-fluorophenyl | Me | H | H | 2-n-propyl-6-iodophenyl |
| 281 | 4-fluorophenyl | Me | H | H | 2-n-propyl-6-iodophenyl |
| 282 | 2-chlorophenyl | Me | H | H | 2-n-propyl-6-iodophenyl |
| 283 | 4-chlorophenyl | Me | H | H | 2-n-propyl-6-iodophenyl |
| 284 | 2-bromophenyl | Me | H | H | 2-n-propyl-6-iodophenyl |
| 285 | 2-iodophenyl | Me | H | H | 2-n-propyl-6-iodophenyl |
| 286 | 3-cyanophenyl | Me | H | H | 2-n-propyl-6-iodophenyl |
| 287 | 4-cyanophenyl | Me | H | H | 2-n-propyl-6-iodophenyl |
| 288 | 2-nitrophenyl | Me | H | H | 2-n-propyl-6-iodophenyl |
| 289 | 3-nitrophenyl | Me | H | H | 2-n-propyl-6-iodophenyl |
| 290 | 4-nitrophenyl | Me | H | H | 2-n-propyl-6-iodophenyl |
| 291 | 2-trifluoromethylphenyl | Me | H | H | 2-n-propyl-6-iodophenyl |
| 292 | 4-trifluoromethylphenyl | Me | H | H | 2-n-propyl-6-iodophenyl |
| 293 | 4-trifluoromethoxyphenyl | Me | H | H | 2-n-propyl-6-iodophenyl |
| 294 | 2,3-difluorophenyl | Me | H | H | 2-n-propyl-6-iodophenyl |
| 295 | 2,4-difluorophenyl | Me | H | H | 2-n-propyl-6-iodophenyl |
| 296 | 2,5-difluorophenyl | Me | H | H | 2-n-propyl-6-iodophenyl |
| 297 | 2,6-difluorophenyl | Me | H | H | 2-n-propyl-6-iodophenyl |
| 298 | 2,4-dichlorophenyl | Me | H | H | 2-n-propyl-6-iodophenyl |
| 299 | 2,6-dichlorophenyl | Me | H | H | 2-n-propyl-6-iodophenyl |
| 300 | 3,4-dichlorophenyl | Me | H | H | 2-n-propyl-6-iodophenyl |
| 301 | 2-chloro-4-nitrophenyl | Me | H | H | 2-n-propyl-6-iodophenyl |
| 302 | 2-chloro-4-fluorophenyl | Me | H | H | 2-n-propyl-6-iodophenyl |
| 303 | 2-chloro-6-fluorophenyl | Me | H | H | 2-n-propyl-6-iodophenyl |
| 304 | 4-chloro-2-fluorophenyl | Me | H | H | 2-n-propyl-6-iodophenyl |
| 305 | 4-chloro-2-nitrophenyl | Me | H | H | 2-n-propyl-6-iodophenyl |
| 306 | 2,3,6-trifluorophenyl | Me | H | H | 2-n-propyl-6-iodophenyl |
| 307 | pyridin-2-yl | Me | H | H | 2-n-propyl-6-iodophenyl |

TABLE 3-continued

| Compound No. | Q¹ | R¹ | X¹ | X² | Q² |
|---|---|---|---|---|---|
| 308 | pyridin-3-yl | Me | H | H | 2-n-propyl-6-iodophenyl |
| 309 | 2-fluoropyridin-3-yl | Me | H | H | 2-n-propyl-6-iodophenyl |
| 310 | 2-chloropyridin-3-yl | Me | H | H | 2-n-propyl-6-iodophenyl |
| 311 | 2-chloropyridin-5-yl | Me | H | H | 2-n-propyl-6-iodophenyl |
| 312 | 2-methylthiopyridin-3-yl | Me | H | H | 2-n-propyl-6-iodophenyl |
| 313 | pyrazin-2-yl | Me | H | H | 2-n-propyl-6-iodophenyl |
| 314 | furan-2-yl | Me | H | H | 2-n-propyl-6-iodophenyl |
| 315 | 2-fluorophenyl | Et | H | H | 2,6-dimethylphenyl |
| 316 | pyridin-3-yl | Et | H | H | 2,6-dimethylphenyl |
| 317 | phenyl | Me | F | H | 2,6-dimethylphenyl |
| 318 | 2-methylphenyl | Me | F | H | 2,6-dimethylphenyl |
| 319 | 3-methylphenyl | Me | F | H | 2,6-dimethylphenyl |
| 320 | 4-methylphenyl | Me | F | H | 2,6-dimethylphenyl |
| 321 | 2-nitrophenyl | Me | F | H | 2,6-dimethylphenyl |
| 322 | 3-nitrophenyl | Me | F | H | 2,6-dimethylphenyl |
| 323 | 4-nitrophenyl | Me | F | H | 2,6-dimethylphenyl |
| 324 | 2-cyanophenyl | Me | F | H | 2,6-dimethylphenyl |
| 325 | 3-cyanophenyl | Me | F | H | 2,6-dimethylphenyl |
| 326 | 4-cyanophenyl | Me | F | H | 2,6-dimethylphenyl |
| 327 | 2-fluorophenyl | Me | F | H | 2,6-dimethylphenyl |
| 328 | 3-fluorophenyl | Me | F | H | 2,6-dimethylphenyl |
| 329 | 4-fluorophenyl | Me | F | H | 2,6-dimethylphenyl |
| 330 | 2-chlorophenyl | Me | F | H | 2,6-dimethylphenyl |
| 331 | 4-chlorophenyl | Me | F | H | 2,6-dimethylphenyl |
| 332 | 2-bromophenyl | Me | F | H | 2,6-dimethylphenyl |
| 333 | 2-iodophenyl | Me | F | H | 2,6-dimethylphenyl |
| 334 | 2-trifluoromethylphenyl | Me | F | H | 2,6-dimethylphenyl |
| 335 | 4-trifluoromethylphenyl | Me | F | H | 2,6-dimethylphenyl |
| 336 | 4-trifluoromethoxyphenyl | Me | F | H | 2,6-dimethylphenyl |
| 337 | 2,3-difluorophenyl | Me | F | H | 2,6-dimethylphenyl |
| 338 | 2,4-difluorophenyl | Me | F | H | 2,6-dimethylphenyl |
| 339 | 2,5-difluorophenyl | Me | F | H | 2,6-dimethylphenyl |
| 340 | 2,6-difluorophenyl | Me | F | H | 2,6-dimethylphenyl |
| 341 | 2,4-dichlorophenyl | Me | F | H | 2,6-dimethylphenyl |
| 342 | 2,6-dichlorophenyl | Me | F | H | 2,6-dimethylphenyl |
| 343 | 3,4-dichlorophenyl | Me | F | H | 2,6-dimethylphenyl |
| 344 | 2-fluoro-4-nitrophenyl | Me | F | H | 2,6-dimethylphenyl |
| 345 | 4-fluoro-2-nitrophenyl | Me | F | H | 2,6-dimethylphenyl |
| 346 | 2-chloro-4-fluorophenyl | Me | F | H | 2,6-dimethylphenyl |
| 347 | 4-chloro-2-fluorophenyl | Me | F | H | 2,6-dimethylphenyl |
| 348 | 2-chloro-6-fluorophenyl | Me | F | H | 2,6-dimethylphenyl |
| 349 | 2-chloro-4-nitrophenyl | Me | F | H | 2,6-dimethylphenyl |
| 350 | 4-chloro-2-nitrophenyl | Me | F | H | 2,6-dimethylphenyl |
| 351 | 2,3,6-trifluorophenyl | Me | F | H | 2,6-dimethylphenyl |
| 352 | pyridin-2-yl | Me | F | H | 2,6-dimethylphenyl |
| 353 | pyridin-3-yl | Me | F | H | 2,6-dimethylphenyl |
| 354 | 2-chloropyridin-3-yl | Me | F | H | 2,6-dimethylphenyl |
| 355 | 2-fluoropyridin-3-yl | Me | F | H | 2,6-dimethylphenyl |
| 356 | 2-chloropyridin-5-yl | Me | F | H | 2,6-dimethylphenyl |
| 357 | 2-methylthiopyridin-3-yl | Me | F | H | 2,6-dimethylphenyl |
| 358 | pyrazin-2-yl | Me | F | H | 2,6-dimethylphenyl |
| 359 | furan-2-yl | Me | F | H | 2,6-dimethylphenyl |
| 360 | furan-3-yl | Me | F | H | 2,6-dimethylphenyl |
| 361 | 2-tetrahydrofuranyl | Me | F | H | 2,6-dimethylphenyl |
| 362 | benzofuran-2-yl | Me | F | H | 2,6-dimethylphenyl |
| 363 | thiophen-2-yl | Me | F | H | 2,6-dimethylphenyl |
| 364 | phenyl | Me | F | H | 2-bromo-6-(methylsulfonyl)phenyl |
| 365 | 2-methylphenyl | Me | F | H | 2-bromo-6-(methylsulfonyl)phenyl |
| 366 | 4-methylphenyl | Me | F | H | 2-bromo-6-(methylsulfonyl)phenyl |
| 367 | 2-fluorophenyl | Me | F | H | 2-bromo-6-(methylsulfonyl)phenyl |
| 368 | 3-fluorophenyl | Me | F | H | 2-bromo-6-(methylsulfonyl)phenyl |
| 369 | 4-fluorophenyl | Me | F | H | 2-bromo-6-(methylsulfonyl)phenyl |
| 370 | 2-chlorophenyl | Me | F | H | 2-bromo-6-(methylsulfonyl)phenyl |
| 371 | 4-chlorophenyl | Me | F | H | 2-bromo-6-(methylsulfonyl)phenyl |
| 372 | 2-bromophenyl | Me | F | H | 2-bromo-6-(methylsulfonyl)phenyl |
| 373 | 2-iodophenyl | Me | F | H | 2-bromo-6-(methylsulfonyl)phenyl |
| 374 | 3-cyanophenyl | Me | F | H | 2-bromo-6-(methylsulfonyl)phenyl |

TABLE 3-continued

| Compound No. | Q¹ | R¹ | X¹ | X² | Q² |
|---|---|---|---|---|---|
| 375 | 4-cyanophenyl | Me | F | H | 2-bromo-6-(methylsulfonyl)phenyl |
| 376 | 2-nitrophenyl | Me | F | H | 2-bromo-6-(methylsulfonyl)phenyl |
| 377 | 3-nitrophenyl | Me | F | H | 2-bromo-6-(methylsulfonyl)phenyl |
| 378 | 4-nitrophenyl | Me | F | H | 2-bromo-6-(methylsulfonyl)phenyl |
| 379 | 2-trifluoromethylphenyl | Me | F | H | 2-bromo-6-(methylsulfonyl)phenyl |
| 380 | 4-trifluoromethylphenyl | Me | F | H | 2-bromo-6-(methylsulfonyl)phenyl |
| 381 | 4-trifluoromethoxyphenyl | Me | F | H | 2-bromo-6-(methylsulfonyl)phenyl |
| 382 | 2,3-difluorophenyl | Me | F | H | 2-bromo-6-(methylsulfonyl)phenyl |
| 383 | 2,4-difluorophenyl | Me | F | H | 2-bromo-6-(methylsulfonyl)phenyl |
| 384 | 2,5-difluorophenyl | Me | F | H | 2-bromo-6-(methylsulfonyl)phenyl |
| 385 | 2,6-difluorophenyl | Me | F | H | 2-bromo-6-(methylsulfonyl)phenyl |
| 386 | 2,4-dichlorophenyl | Me | F | H | 2-bromo-6-(methylsulfonyl)phenyl |
| 387 | 2,6-dichlorophenyl | Me | F | H | 2-bromo-6-(methylsulfonyl)phenyl |
| 388 | 3,4-dichlorophenyl | Me | F | H | 2-bromo-6-(methylsulfonyl)phenyl |
| 389 | 2-chloro-4-nitrophenyl | Me | F | H | 2-bromo-6-(methylsulfonyl)phenyl |
| 390 | 2-chloro-4-fluorophenyl | Me | F | H | 2-bromo-6-(methylsulfonyl)phenyl |
| 391 | 2-chloro-6-fluorophenyl | Me | F | H | 2-bromo-6-(methylsulfonyl)phenyl |
| 392 | 4-chloro-2-fluorophenyl | Me | F | H | 2-bromo-6-(methylsulfonyl)phenyl |
| 393 | 4-chloro-2-nitrophenyl | Me | F | H | 2-bromo-6-(methylsulfonyl)phenyl |
| 394 | 2,3,6-trifluorophenyl | Me | F | H | 2-bromo-6-(methylsulfonyl)phenyl |
| 395 | pyridin-2-yl | Me | F | H | 2-bromo-6-(methylsulfonyl)phenyl |
| 396 | pyridin-3-yl | Me | F | H | 2-bromo-6-(methylsulfonyl)phenyl |
| 397 | 2-fluoropyridin-3-yl | Me | F | H | 2-bromo-6-(methylsulfonyl)phenyl |
| 398 | 2-chloropyridin-3-yl | Me | F | H | 2-bromo-6-(methylsulfonyl)phenyl |
| 399 | 2-chloropyridin-5-yl | Me | F | H | 2-bromo-6-(methylsulfonyl)phenyl |
| 400 | 2-methylthiopyridin-3-yl | Me | F | H | 2-bromo-6-(methylsulfonyl)phenyl |
| 401 | pyrazin-2-yl | Me | F | H | 2-bromo-6-(methylsulfonyl)phenyl |
| 402 | furan-2-yl | Me | F | H | 2-bromo-6-(methylsulfonyl)phenyl |
| 403 | thiophen-2-yl | Me | F | H | 2-bromo-6-(methylsulfonyl)phenyl |
| 404 | phenyl | Me | F | H | 2-n-propyl-6-iodophenyl |
| 405 | 2-methylphenyl | Me | F | H | 2-n-propyl-6-iodophenyl |
| 406 | 4-methylphenyl | Me | F | H | 2-n-propyl-6-iodophenyl |
| 407 | 2-fluorophenyl | Me | F | H | 2-n-propyl-6-iodophenyl |
| 408 | 3-fluorophenyl | Me | F | H | 2-n-propyl-6-iodophenyl |
| 409 | 4-fluorophenyl | Me | F | H | 2-n-propyl-6-iodophenyl |
| 410 | 2-chlorophenyl | Me | F | H | 2-n-propyl-6-iodophenyl |
| 411 | 4-chlorophenyl | Me | F | H | 2-n-propyl-6-iodophenyl |
| 412 | 2-bromophenyl | Me | F | H | 2-n-propyl-6-iodophenyl |
| 413 | 2-iodophenyl | Me | F | H | 2-n-propyl-6-iodophenyl |
| 414 | 3-cyanophenyl | Me | F | H | 2-n-propyl-6-iodophenyl |
| 415 | 4-cyanophenyl | Me | F | H | 2-n-propyl-6-iodophenyl |
| 416 | 2-nitrophenyl | Me | F | H | 2-n-propyl-6-iodophenyl |
| 417 | 3-nitrophenyl | Me | F | H | 2-n-propyl-6-iodophenyl |
| 418 | 4-nitrophenyl | Me | F | H | 2-n-propyl-6-iodophenyl |
| 419 | 2-trifluoromethylphenyl | Me | F | H | 2-n-propyl-6-iodophenyl |
| 420 | 4-trifluoromethylphenyl | Me | F | H | 2-n-propyl-6-iodophenyl |
| 421 | 4-trifluoromethoxyphenyl | Me | F | H | 2-n-propyl-6-iodophenyl |
| 422 | 2,3-difluorophenyl | Me | F | H | 2-n-propyl-6-iodophenyl |
| 423 | 2,4-difluorophenyl | Me | F | H | 2-n-propyl-6-iodophenyl |

TABLE 3-continued

| Compound No. | $Q^1$ | $R^1$ | $X^1$ | $X^2$ | $Q^2$ |
|---|---|---|---|---|---|
| 424 | 2,5-difluorophenyl | Me | F | H | 2-n-propyl-6-iodophenyl |
| 425 | 2,6-difluorophenyl | Me | F | H | 2-n-propyl-6-iodophenyl |
| 426 | 2,4-dichlorophenyl | Me | F | H | 2-n-propyl-6-iodophenyl |
| 427 | 2,6-dichlorophenyl | Me | F | H | 2-n-propyl-6-iodophenyl |
| 428 | 3,4-dichlorophenyl | Me | F | H | 2-n-propyl-6-iodophenyl |
| 429 | 2-chloro-4-nitrophenyl | Me | F | H | 2-n-propyl-6-iodophenyl |
| 430 | 2-chloro-4-fluorophenyl | Me | F | H | 2-n-propyl-6-iodophenyl |
| 431 | 2-chloro-6-fluorophenyl | Me | F | H | 2-n-propyl-6-iodophenyl |
| 432 | 4-chloro-3-fluorophenyl | Me | F | H | 2-n-propyl-6-iodophenyl |
| 433 | 4-chloro-2-nitrophenyl | Me | F | H | 2-n-propyl-6-iodophenyl |
| 434 | 2,3,6-trifluorophenyl | Me | F | H | 2-n-propyl-6-iodophenyl |
| 435 | pyridin-2-yl | Me | F | H | 2-n-propyl-6-iodophenyl |
| 436 | pyridin-3-yl | Me | F | H | 2-n-propyl-6-iodophenyl |
| 437 | 2-fluoropyridin-3-yl | Me | F | H | 2-n-propyl-6-iodophenyl |
| 438 | 2-chloropyridin-3-yl | Me | F | H | 2-n-propyl-6-iodophenyl |
| 439 | 2-chloropyridin-5-yl | Me | F | H | 2-n-propyl-6-iodophenyl |
| 440 | 2-methylthiopyridin-3-yl | Me | F | H | 2-n-propyl-6-iodophenyl |
| 441 | pyrazin-2-yl | Me | F | H | 2-n-propyl-6-iodophenyl |
| 442 | furan-2-yl | Me | F | H | 2-n-propyl-6-iodophenyl |
| 443 | thiophen-2-yl | Me | F | H | 2-n-propyl-6-iodophenyl |
| 444 | phenyl | Et | F | H | 2,6-dimethylphenyl |
| 445 | phenyl | Me | H | F | 2,6-dimethylphenyl |
| 446 | 4-nitrophenyl | Me | H | F | 2,6-dimethylphenyl |
| 447 | 4-cyanophenyl | Me | H | F | 2,6-dimethylphenyl |
| 448 | phenyl | Me | H | F | 2-bromo-6-(methylsulfonyl)phenyl |
| 449 | 4-nitrophenyl | Me | H | F | 2-bromo-6-(methylsulfonyl)phenyl |
| 450 | 4-cyanophenyl | Me | H | F | 2-bromo-6-(methylsulfonyl)phenyl |
| 451 | phenyl | Me | H | F | 2-n-propyl-6-iodophenyl |
| 452 | 4-nitrophenyl | Me | H | F | 2-n-propyl-6-iodophenyl |
| 453 | 4-cyanophenyl | Me | H | F | 2-n-propyl-6-iodophenyl |
| 454 | phenyl | Me | H | H | 2-trifluoromethylphenyl |
| 455 | 2-fluorophenyl | Me | H | H | 2-trifluoromethylphenyl |
| 456 | 4-fluorophenyl | Me | H | H | 2-trifluoromethylphenyl |
| 457 | 4-nitrophenyl | Me | H | H | 2-trifluoromethylphenyl |
| 458 | 4-cyanophenyl | Me | H | H | 2-trifluoromethylphenyl |
| 459 | 2-chloropyridin-3-yl | Me | H | H | 2-trifluoromethylphenyl |
| 460 | phenyl | Me | H | H | 2-pentafluoroethylphenyl |
| 461 | 2-fluorophenyl | Me | H | H | 2-pentafluoroethylphenyl |
| 462 | 4-fluorophenyl | Me | H | H | 2-pentafluoroethylphenyl |
| 463 | 4-nitrophenyl | Me | H | H | 2-pentafluoroethylphenyl |
| 464 | 4-cyanophenyl | Me | H | H | 2-pentafluoroethylphenyl |
| 465 | 2-chloropyridin-3-yl | Me | H | H | 2-pentafluoroethylphenyl |
| 466 | phenyl | Me | H | H | 2-methylphenyl |
| 467 | 2-fluorophenyl | Me | H | H | 2-methylphenyl |
| 468 | 4-fluorophenyl | Me | H | H | 2-methylphenyl |
| 469 | 4-nitrophenyl | Me | H | H | 2-methylphenyl |
| 470 | 4-cyanophenyl | Me | H | H | 2-methylphenyl |
| 471 | 2-chloropyridin-3-yl | Me | H | H | 2-methylphenyl |
| 472 | phenyl | Me | H | H | 2-fluorophenyl |
| 473 | 2-fluorophenyl | Me | H | H | 2-fluorophenyl |
| 474 | 4-fluorophenyl | Me | H | H | 2-fluorophenyl |
| 475 | 4-nitrophenyl | Me | H | H | 2-fluorophenyl |
| 476 | 4-cyanophenyl | Me | H | H | 2-fluorophenyl |
| 477 | 2-chloropyridin-3-yl | Me | H | H | 2-fluorophenyl |
| 478 | phenyl | Me | H | H | 2-chlorophenyl |
| 479 | 2-fluorophenyl | Me | H | H | 2-chlorophenyl |
| 480 | 4-fluorophenyl | Me | H | H | 2-chlorophenyl |
| 481 | 4-nitrophenyl | Me | H | H | 2-chlorophenyl |
| 482 | 4-cyanophenyl | Me | H | H | 2-chlorophenyl |
| 483 | 2-chloropyridin-3-yl | Me | H | H | 2-chlorophenyl |
| 484 | phenyl | Me | H | H | 2-bromophenyl |
| 485 | 2-fluorophenyl | Me | H | H | 2-bromophenyl |
| 486 | 4-fluorophenyl | Me | H | H | 2-bromophenyl |
| 487 | 4-nitrophenyl | Me | H | H | 2-bromophenyl |
| 488 | 4-cyanophenyl | Me | H | H | 2-bromophenyl |
| 489 | 2-chloropyridin-3-yl | Me | H | H | 2-bromophenyl |
| 490 | phenyl | Me | H | H | 2-iodophenyl |
| 491 | 2-fluorophenyl | Me | H | H | 2-iodophenyl |
| 492 | 4-fluorophenyl | Me | H | H | 2-iodophenyl |
| 493 | 4-nitrophenyl | Me | H | H | 2-iodophenyl |
| 494 | 4-cyanophenyl | Me | H | H | 2-iodophenyl |
| 495 | 2-chloropyridin-3-yl | Me | H | H | 2-iodophenyl |
| 496 | phenyl | Me | H | H | 2-iodophenyl |
| 497 | 2-fluorophenyl | Me | H | H | 2-iodophenyl |
| 498 | 4-fluorophenyl | Me | H | H | 2-iodophenyl |

TABLE 3-continued

| Compound No. | Q¹ | R¹ | X¹ | X² | Q² |
|---|---|---|---|---|---|
| 499 | 4-nitrophenyl | Me | H | H | 2-iodophenyl |
| 500 | 4-cyanophenyl | Me | H | H | 2-iodophenyl |
| 501 | 2-chloropyridin-3-yl | Me | H | H | 2-iodophenyl |
| 502 | phenyl | Me | H | H | 2-trifluoromethylthiophenyl |
| 503 | 2-fluorophenyl | Me | H | H | 2-trifluoromethylthiophenyl |
| 504 | 4-fluorophenyl | Me | H | H | 2-trifluoromethylthiophenyl |
| 505 | 4-nitrophenyl | Me | H | H | 2-trifluoromethylthiophenyl |
| 506 | 4-cyanophenyl | Me | H | H | 2-trifluoromethylthiophenyl |
| 507 | 2-chloropyridin-3-yl | Me | H | H | 2-trifluoromethylthiophenyl |
| 508 | phenyl | Et | H | H | 2-trifluoromethylphenyl |
| 509 | phenyl | Me | F | H | 2-trifluoromethylphenyl |
| 510 | 2-fluorophenyl | Me | F | H | 2-trifluoromethylphenyl |
| 511 | 4-fluorophenyl | Me | F | H | 2-trifluoromethylphenyl |
| 512 | 4-nitrophenyl | Me | F | H | 2-trifluoromethylphenyl |
| 513 | 4-cyanophenyl | Me | F | H | 2-trifluoromethylphenyl |
| 514 | 2-chloropyridin-3-yl | Me | F | H | 2-trifluoromethylphenyl |
| 515 | phenyl | Me | F | H | 2-pentafluoroethylphenyl |
| 516 | 2-fluorophenyl | Me | F | H | 2-pentafluoroethylphenyl |
| 517 | 4-fluorophenyl | Me | F | H | 2-pentafluoroethylphenyl |
| 518 | 4-nitrophenyl | Me | F | H | 2-pentafluoroethylphenyl |
| 519 | 4-cyanophenyl | Me | F | H | 2-pentafluoroethylphenyl |
| 520 | 2-chloropyridin-3-yl | Me | F | H | 2-pentafluoroethylphenyl |
| 521 | phenyl | Me | F | H | 2-methylphenyl |
| 522 | 2-fluorophenyl | Me | F | H | 2-methylphenyl |
| 523 | 4-fluorophenyl | Me | F | H | 2-methylphenyl |
| 524 | 4-nitrophenyl | Me | F | H | 2-methylphenyl |
| 525 | 4-cyanophenyl | Me | F | H | 2-methylphenyl |
| 526 | 2-chloropyridin-3-yl | Me | F | H | 2-methylphenyl |
| 527 | phenyl | Me | F | H | 2-fluorophenyl |
| 528 | 2-fluorophenyl | Me | F | H | 2-fluorophenyl |
| 529 | 4-fluorophenyl | Me | F | H | 2-fluorophenyl |
| 530 | 4-nitrophenyl | Me | F | H | 2-fluorophenyl |
| 531 | 4-cyanophenyl | Me | F | H | 2-fluorophenyl |
| 532 | 2-chloropyridin-3-yl | Me | F | H | 2-fluorophenyl |
| 533 | phenyl | Me | F | H | 2-chlorophenyl |
| 534 | 2-fluorophenyl | Me | F | H | 2-chlorophenyl |
| 535 | 4-fluorophenyl | Me | F | H | 2-chlorophenyl |
| 536 | 4-nitrophenyl | Me | F | H | 2-chlorophenyl |
| 537 | 4-cyanophenyl | Me | F | H | 2-chlorophenyl |
| 538 | 2-chloropyridin-3-yl | Me | F | H | 2-chlorophenyl |
| 539 | phenyl | Me | F | H | 2-bromophenyl |
| 540 | 2-fluorophenyl | Me | F | H | 2-bromophenyl |
| 541 | 4-fluorophenyl | Me | F | H | 2-bromophenyl |
| 542 | 4-nitrophenyl | Me | F | H | 2-bromophenyl |
| 543 | 4-cyanophenyl | Me | F | H | 2-bromophenyl |
| 544 | 2-chloropyridin-3-yl | Me | F | H | 2-bromophenyl |
| 545 | phenyl | Me | F | H | 2-iodophenyl |
| 546 | 2-fluorophenyl | Me | F | H | 2-iodophenyl |
| 547 | 4-fluorophenyl | Me | F | H | 2-iodophenyl |
| 548 | 4-nitrophenyl | Me | F | H | 2-iodophenyl |
| 549 | 4-cyanophenyl | Me | F | H | 2-iodophenyl |
| 550 | 2-chloropyridin-3-yl | Me | F | H | 2-iodophenyl |
| 551 | phenyl | Me | F | H | 2-iodophenyl |
| 552 | 2-fluorophenyl | Me | F | H | 2-iodophenyl |
| 553 | 4-fluorophenyl | Me | F | H | 2-iodophenyl |
| 554 | 4-nitrophenyl | Me | F | H | 2-iodophenyl |
| 555 | 4-cyanophenyl | Me | F | H | 2-iodophenyl |
| 556 | 2-chloropyridin-3-yl | Me | F | H | 2-iodophenyl |
| 557 | phenyl | Me | F | H | 2-trifluoromethylthiophenyl |
| 558 | 2-fluorophenyl | Me | F | H | 2-trifluoromethylthiophenyl |
| 559 | 4-fluorophenyl | Me | F | H | 2-trifluoromethylthiophenyl |
| 560 | 4-nitrophenyl | Me | F | H | 2-trifluoromethylthiophenyl |

Hereinafter, the representative compounds among the compounds represented by Formula (9), which are the effective intermediates according to the invention, are shown in Table 4 to Table 5, but the invention is not limited thereto.

In the tables, "Me" represents a methyl group, "Et" represents an ethyl group, "H" represents a hydrogen atom, "F" represents a fluorine atom, "Cl" represents a chlorine atom, "Br" represents a bromine atom, "I" represents an iodine atom, and "CF3" represents a trifluoromethyl group.

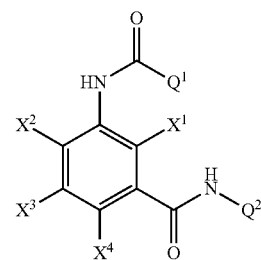

TABLE 4

| Compound No. | Q¹ | X¹ | X² | X³ | X⁴ | Q² |
|---|---|---|---|---|---|---|
| 561 | phenyl | F | H | H | H | 2-trifluoromethyl-4-(heptafluoroisopropyl)phenyl |
| 562 | 2-fluorophenyl | F | H | H | H | 2-trifluoromethyl-4-(heptafluoroisopropyl)phenyl |
| 563 | 4-fluorophenyl | F | H | H | H | 2-trifluoromethyl-4-(heptafluoroisopropyl)phenyl |
| 564 | 4-nitrophenyl | F | H | H | H | 2-trifluoromethyl-4-(heptafluoroisopropyl)phenyl |
| 565 | 4-cyanophenyl | F | H | H | H | 2-trifluoromethyl-4-(heptafluoroisopropyl)phenyl |
| 566 | 2-chloropyridin-3-yl | F | H | H | H | 2-trifluoromethyl-4-(heptafluoroisopropyl)phenyl |
| 567 | phenyl | H | H | CF3 | H | 2-trifluoromethyl-4-(heptafluoroisopropyl)phenyl |
| 568 | phenyl | H | H | H | F | 2-trifluoromethyl-4-(heptafluoroisopropyl)phenyl |
| 569 | phenyl | H | H | H | Cl | 2-trifluoromethyl-4-(heptafluoroisopropyl)phenyl |
| 570 | phenyl | H | H | H | Br | 2-trifluoromethyl-4-(heptafluoroisopropyl)phenyl |
| 571 | phenyl | H | H | H | I | 2-trifluoromethyl-4-(heptafluoroisopropyl)phenyl |
| 572 | phenyl | F | H | H | F | 2-trifluoromethyl-4-(heptafluoroisopropyl)phenyl |
| 573 | phenyl | H | Br | H | Br | 2-trifluoromethyl-4-(heptafluoroisopropyl)phenyl |
| 574 | phenyl | F | H | H | H | 2-pentafluoroethyl-4-(heptafluoroisopropyl)phenyl |
| 575 | 2-fluorophenyl | F | H | H | H | 2-pentafluoroethyl-4-(heptafluoroisopropyl)phenyl |
| 576 | 4-fluorophenyl | F | H | H | H | 2-pentafluoroethyl-4-(heptafluoroisopropyl)phenyl |
| 577 | 4-nitrophenyl | F | H | H | H | 2-pentafluoroethyl-4-(heptafluoroisopropyl)phenyl |
| 578 | 4-cyanophenyl | F | H | H | H | 2-pentafluoroethyl-4-(heptafluoroisopropyl)phenyl |
| 579 | 2-chloropyridin-3-yl | F | H | H | H | 2-pentafluoroethyl-4-(heptafluoroisopropyl)phenyl |
| 580 | phenyl | F | H | H | H | 2-methyl-4-(heptafluoroisopropyl)phenyl |
| 581 | 2-fluorophenyl | F | H | H | H | 2-methyl-4-(heptafluoroisopropyl)phenyl |
| 582 | 4-fluorophenyl | F | H | H | H | 2-methyl-4-(heptafluoroisopropyl)phenyl |
| 583 | 4-nitrophenyl | F | H | H | H | 2-methyl-4-(heptafluoroisopropyl)phenyl |
| 584 | 4-cyanophenyl | F | H | H | H | 2-methyl-4-(heptafluoroisopropyl)phenyl |
| 585 | 2-chloropyridin-3-yl | F | H | H | H | 2-methyl-4-(heptafluoroisopropyl)phenyl |
| 586 | phenyl | F | H | H | H | 2-fluoro-4-(heptafluoroisopropyl)phenyl |
| 587 | 2-fluorophenyl | F | H | H | H | 2-fluoro-4-(heptafluoroisopropyl)phenyl |
| 588 | 4-fluorophenyl | F | H | H | H | 2-fluoro-4-(heptafluoroisopropyl)phenyl |
| 589 | 4-nitrophenyl | F | H | H | H | 2-fluoro-4-(heptafluoroisopropyl)phenyl |
| 590 | 4-cyanophenyl | F | H | H | H | 2-fluoro-4-(heptafluoroisopropyl)phenyl |
| 591 | 2-chloropyridin-3-yl | F | H | H | H | 2-fluoro-4-(heptafluoroisopropyl)phenyl |
| 592 | phenyl | F | H | H | H | 2-chloro-4-(heptafluoroisopropyl)phenyl |
| 593 | 2-fluorophenyl | F | H | H | H | 2-chloro-4-(heptafluoroisopropyl)phenyl |
| 594 | 4-fluorophenyl | F | H | H | H | 2-chloro-4-(heptafluoroisopropyl)phenyl |
| 595 | 4-nitrophenyl | F | H | H | H | 2-chloro-4-(heptafluoroisopropyl)phenyl |
| 596 | 4-cyanophenyl | F | H | H | H | 2-chloro-4-(heptafluoroisopropyl)phenyl |
| 597 | 2-chloropyridin-3-yl | F | H | H | H | 2-chloro-4-(heptafluoroisopropyl)phenyl |
| 598 | phenyl | F | H | H | H | 2-bromo-4-(heptafluoroisopropyl)phenyl |
| 599 | 2-fluorophenyl | F | H | H | H | 2-bromo-4-(heptafluoroisopropyl)phenyl |
| 600 | 4-fluorophenyl | F | H | H | H | 2-bromo-4-(heptafluoroisopropyl)phenyl |
| 601 | 4-nitrophenyl | F | H | H | H | 2-bromo-4-(heptafluoroisopropyl)phenyl |

TABLE 4-continued

| Compound No. | Q¹ | X¹ | X² | X³ | X⁴ | Q² |
|---|---|---|---|---|---|---|
| 602 | 4-cyanophenyl | F | H | H | H | 2-bromo-4-(heptafluoroisopropyl)phenyl |
| 603 | 2-chloropyridin-3-yl | F | H | H | H | 2-bromo-4-(heptafluoroisopropyl)phenyl |
| 604 | phenyl | F | H | H | H | 2-iodo-4-(heptafluoroisopropyl)phenyl |
| 605 | 2-fluorophenyl | F | H | H | H | 2-iodo-4-(heptafluoroisopropyl)phenyl |
| 606 | 4-fluorophenyl | F | H | H | H | 2-iodo-4-(heptafluoroisopropyl)phenyl |
| 607 | 4-nitrophenyl | F | H | H | H | 2-iodo-4-(heptafluoroisopropyl)phenyl |
| 608 | 4-cyanophenyl | F | H | H | H | 2-iodo-4-(heptafluoroisopropyl)phenyl |
| 609 | 2-chloropyridin-3-yl | F | H | H | H | 2-iodo-4-(heptafluoroisopropyl)phenyl |
| 610 | phenyl | F | H | H | H | 2-iodo-4-(heptafluoroisopropyl)phenyl |
| 611 | 2-fluorophenyl | F | H | H | H | 2-iodo-4-(heptafluoroisopropyl)phenyl |
| 612 | 4-fluorophenyl | F | H | H | H | 2-iodo-4-(heptafluoroisopropyl)phenyl |
| 613 | 4-nitrophenyl | F | H | H | H | 2-iodo-4-(heptafluoroisopropyl)phenyl |
| 614 | 4-cyanophenyl | F | H | H | H | 2-iodo-4-(heptafluoroisopropyl)phenyl |
| 615 | 2-chloropyridin-3-yl | F | H | H | H | 2-iodo-4-(heptafluoroisopropyl)phenyl |
| 616 | phenyl | F | H | H | H | 2-trifluoromethylthio-4-(heptafluoroisopropyl)phenyl |
| 617 | 2-fluorophenyl | F | H | H | H | 2-trifluoromethylthio-4-(heptafluoroisopropyl)phenyl |
| 618 | 4-fluorophenyl | F | H | H | H | 2-trifluoromethylthio-4-(heptafluoroisopropyl)phenyl |
| 619 | 4-nitrophenyl | F | H | H | H | 2-trifluoromethylthio-4-(heptafluoroisopropyl)phenyl |
| 620 | 4-cyanophenyl | F | H | H | H | 2-trifluoromethylthio-4-(heptafluoroisopropyl)phenyl |
| 621 | 2-chloropyridin-3-yl | F | H | H | H | 2-trifluoromethylthio-4-(heptafluoroisopropyl)phenyl |

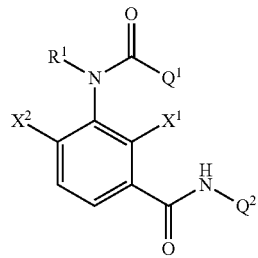

TABLE 5

| Compound No. | Q¹ | R¹ | X¹ | X² | Q² |
|---|---|---|---|---|---|
| 622 | phenyl | Me | H | H | 2-trifluoromethyl-4-(heptafluoroisopropyl)phenyl |
| 623 | 2-fluorophenyl | Me | H | H | 2-trifluoromethyl-4-(heptafluoroisopropyl)phenyl |
| 624 | 4-fluorophenyl | Me | H | H | 2-trifluoromethyl-4-(heptafluoroisopropyl)phenyl |
| 625 | 4-nitrophenyl | Me | H | H | 2-trifluoromethyl-4-(heptafluoroisopropyl)phenyl |
| 626 | 4-cyanophenyl | Me | H | H | 2-trifluoromethyl-4-(heptafluoroisopropyl)phenyl |
| 627 | 2-chloropyridin-3-yl | Me | H | H | 2-trifluoromethyl-4-(heptafluoroisopropyl)phenyl |
| 628 | phenyl | Me | H | H | 2-pentafluoroethyl-4-(heptafluoroisopropyl)phenyl |
| 629 | 2-fluorophenyl | Me | H | H | 2-pentafluoroethyl-4-(heptafluoroisopropyl)phenyl |
| 630 | 4-fluorophenyl | Me | H | H | 2-pentafluoroethyl-4-(heptafluoroisopropyl)phenyl |

TABLE 5-continued

| Compound No. | Q¹ | R¹ | X¹ | X² | Q² |
|---|---|---|---|---|---|
| 631 | 4-nitrophenyl | Me | H | H | 2-pentafluoroethyl-4-(hepta-fluoroisopropyl)phenyl |
| 632 | 4-cyanophenyl | Me | H | H | 2-pentafluoroethyl-4-(hepta-fluoroisopropyl)phenyl |
| 633 | 2-chloropyridin-3-yl | Me | H | H | 2-pentafluoroethyl-4-(hepta-fluoroisopropyl)phenyl |
| 634 | phenyl | Me | H | H | 2-methyl-4-(heptafluoroiso-propyl)phenyl |
| 635 | 2-fluorophenyl | Me | H | H | 2-methyl-4-(heptafluoroiso-propyl)phenyl |
| 636 | 4-fluorophenyl | Me | H | H | 2-methyl-4-(heptafluoroiso-propyl)phenyl |
| 637 | 4-nitrophenyl | Me | H | H | 2-methyl-4-(heptafluoroiso-propyl)phenyl |
| 638 | 4-cyanophenyl | Me | H | H | 2-methyl-4-(heptafluoroiso-propyl)phenyl |
| 639 | 2-chloropyridin-3-yl | Me | H | H | 2-methyl-4-(heptafluoroiso-propyl)phenyl |
| 640 | phenyl | Me | H | H | 2-fluoro-4-(heptafluoroiso-propyl)phenyl |
| 641 | 2-fluorophenyl | Me | H | H | 2-fluoro-4-(heptafluoroiso-propyl)phenyl |
| 642 | 4-fluorophenyl | Me | H | H | 2-fluoro-4-(heptafluoroiso-propyl)phenyl |
| 643 | 4-nitrophenyl | Me | H | H | 2-fluoro-4-(heptafluoroiso-propyl)phenyl |
| 644 | 4-cyanophenyl | Me | H | H | 2-fluoro-4-(heptafluoroiso-propyl)phenyl |
| 645 | 2-chloropyridin-3-yl | Me | H | H | 2-fluoro-4-(heptafluoroiso-propyl)phenyl |
| 646 | phenyl | Me | H | H | 2-chloro-4-(heptafluoroiso-propyl)phenyl |
| 647 | 2-fluorophenyl | Me | H | H | 2-chloro-4-(heptafluoroiso-propyl)phenyl |
| 648 | 4-fluorophenyl | Me | H | H | 2-chloro-4-(heptafluoroiso-propyl)phenyl |
| 649 | 4-nitrophenyl | Me | H | H | 2-chloro-4-(heptafluoroiso-propyl)phenyl |
| 650 | 4-cyanophenyl | Me | H | H | 2-chloro-4-(heptafluoroiso-propyl)phenyl |
| 651 | 2-chloropyridin-3-yl | Me | H | H | 2-chloro-4-(heptafluoroiso-propyl)phenyl |
| 652 | phenyl | Me | H | H | 2-bromo-4-(heptafluoroiso-propyl)phenyl |
| 653 | 2-fluorophenyl | Me | H | H | 2-bromo-4-(heptafluoroiso-propyl)phenyl |
| 654 | 4-fluorophenyl | Me | H | H | 2-bromo-4-(heptafluoroiso-propyl)phenyl |
| 655 | 4-nitrophenyl | Me | H | H | 2-bromo-4-(heptafluoroiso-propyl)phenyl |
| 656 | 4-cyanophenyl | Me | H | H | 2-bromo-4-(heptafluoroiso-propyl)phenyl |
| 657 | 2-chloropyridin-3-yl | Me | H | H | 2-bromo-4-(heptafluoroiso-propyl)phenyl |
| 658 | phenyl | Me | H | H | 2-iodo-4-(heptafluoroiso-propyl)phenyl |
| 659 | 2-fluorophenyl | Me | H | H | 2-iodo-4-(heptafluoroiso-propyl)phenyl |
| 660 | 4-fluorophenyl | Me | H | H | 2-iodo-4-(heptafluoroiso-propyl)phenyl |
| 661 | 4-nitrophenyl | Me | H | H | 2-iodo-4-(heptafluoroiso-propyl)phenyl |
| 662 | 4-cyanophenyl | Me | H | H | 2-iodo-4-(heptafluoroiso-propyl)phenyl |
| 663 | 2-chloropyridin-3-yl | Me | H | H | 2-iodo-4-(heptafluoroiso-propyl)phenyl |
| 664 | phenyl | Me | H | H | 2-iodo-4-(heptafluoroiso-propyl)phenyl |
| 665 | 2-fluorophenyl | Me | H | H | 2-iodo-4-(heptafluoroiso-propyl)phenyl |
| 666 | 4-fluorophenyl | Me | H | H | 2-iodo-4-(heptafluoroiso-propyl)phenyl |
| 667 | 4-nitrophenyl | Me | H | H | 2-iodo-4-(heptafluoroiso-propyl)phenyl |
| 668 | 4-cyanophenyl | Me | H | H | 2-iodo-4-(heptafluoroiso-propyl)phenyl |
| 669 | 2-chloropyridin-3-yl | Me | H | H | 2-iodo-4-(heptafluoroiso-propyl)phenyl |

TABLE 5-continued

| Compound No. | Q¹ | R¹ | X¹ | X² | Q² |
|---|---|---|---|---|---|
| 670 | phenyl | Me | H | H | 2-trifluoromethylthio-4-(hepta-fluoroisopropyl)phenyl |
| 671 | 2-fluorophenyl | Me | H | H | 2-trifluoromethylthio-4-(hepta-fluoroisopropyl)phenyl |
| 672 | 4-fluorophenyl | Me | H | H | 2-trifluoromethylthio-4-(hepta-fluoroisopropyl)phenyl |
| 673 | 4-nitrophenyl | Me | H | H | 2-trifluoromethylthio-4-(hepta-fluoroisopropyl)phenyl |
| 674 | 4-cyanophenyl | Me | H | H | 2-trifluoromethylthio-4-(hepta-fluoroisopropyl)phenyl |
| 675 | 2-chloropyridin-3-yl | Me | H | H | 2-trifluoromethylthio-4-(hepta-fluoroisopropyl)phenyl |
| 676 | phenyl | Et | H | H | 2-trifluoromethyl-4-(hepta-fluoroisopropyl)phenyl |
| 677 | phenyl | Me | F | H | 2-trifluoromethyl-4-(hepta-fluoroisopropyl)phenyl |
| 678 | 2-fluorophenyl | Me | F | H | 2-trifluoromethyl-4-(hepta-fluoroisopropyl)phenyl |
| 679 | 4-fluorophenyl | Me | F | H | 2-trifluoromethyl-4-(hepta-fluoroisopropyl)phenyl |
| 680 | 4-nitrophenyl | Me | F | H | 2-trifluoromethyl-4-(hepta-fluoroisopropyl)phenyl |
| 681 | 4-cyanophenyl | Me | F | H | 2-trifluoromethyl-4-(hepta-fluoroisopropyl)phenyl |
| 682 | 2-chloropyridin-3-yl | Me | F | H | 2-trifluoromethyl-4-(hepta-fluoroisopropyl)phenyl |
| 683 | phenyl | Me | F | H | 2-pentafluoroethyl-4-(hepta-fluoroisopropyl)phenyl |
| 684 | 2-fluorophenyl | Me | F | H | 2-pentafluoroethyl-4-(hepta-fluoroisopropyl)phenyl |
| 685 | 4-fluorophenyl | Me | F | H | 2-pentafluoroethyl-4-(hepta-fluoroisopropyl)phenyl |
| 686 | 4-nitrophenyl | Me | F | H | 2-pentafluoroethyl-4-(hepta-fluoroisopropyl)phenyl |
| 687 | 4-cyanophenyl | Me | F | H | 2-pentafluoroethyl-4-(hepta-fluoroisopropyl)phenyl |
| 688 | 2-chloropyridin-3-yl | Me | F | H | 2-pentafluoroethyl-4-(hepta-fluoroisopropyl)phenyl |
| 689 | phenyl | Me | F | H | 2-methyl-4-(heptafluoroiso-propyl)phenyl |
| 690 | 2-fluorophenyl | Me | F | H | 2-methyl-4-(heptafluoroiso-propyl)phenyl |
| 691 | 4-fluorophenyl | Me | F | H | 2-methyl-4-(heptafluoroiso-propyl)phenyl |
| 692 | 4-nitrophenyl | Me | F | H | 2-methyl-4-(heptafluoroiso-propyl)phenyl |
| 693 | 4-cyanophenyl | Me | F | H | 2-methyl-4-(heptafluoroiso-propyl)phenyl |
| 694 | 2-chloropyridin-3-yl | Me | F | H | 2-methyl-4-(heptafluoroiso-propyl)phenyl |
| 695 | phenyl | Me | F | H | 2-fluoro-4-(heptafluoroiso-propyl)phenyl |
| 696 | 2-fluorophenyl | Me | F | H | 2-fluoro-4-(heptafluoroiso-propyl)phenyl |
| 697 | 4-fluorophenyl | Me | F | H | 2-fluoro-4-(heptafluoroiso-propyl)phenyl |
| 698 | 4-nitrophenyl | Me | F | H | 2-fluoro-4-(heptafluoroiso-propyl)phenyl |
| 699 | 4-cyanophenyl | Me | F | H | 2-fluoro-4-(heptafluoroiso-propyl)phenyl |
| 700 | 2-chloropyridin-3-yl | Me | F | H | 2-fluoro-4-(heptafluoroiso-propyl)phenyl |
| 701 | phenyl | Me | F | H | 2-chloro-4-(heptafluoroiso-propyl)phenyl |
| 702 | 2-fluorophenyl | Me | F | H | 2-chloro-4-(heptafluoroiso-propyl)phenyl |
| 703 | 4-fluorophenyl | Me | F | H | 2-chloro-4-(heptafluoroiso-propyl)phenyl |
| 704 | 4-nitrophenyl | Me | F | H | 2-chloro-4-(heptafluoroiso-propyl)phenyl |
| 705 | 4-cyanophenyl | Me | F | H | 2-chloro-4-(heptafluoroiso-propyl)phenyl |
| 706 | 2-chloropyridin-3-yl | Me | F | H | 2-chloro-4-(heptafluoroiso-propyl)phenyl |
| 707 | phenyl | Me | F | H | 2-bromo-4-(heptafluoroiso-propyl)phenyl |
| 708 | 2-fluorophenyl | Me | F | H | 2-bromo-4-(heptafluoroiso-propyl)phenyl |

TABLE 5-continued

| Compound No. | Q¹ | R¹ | X¹ | X² | Q² |
|---|---|---|---|---|---|
| 709 | 4-fluorophenyl | Me | F | H | 2-bromo-4-(heptafluoroiso-propyl)phenyl |
| 710 | 4-nitrophenyl | Me | F | H | 2-bromo-4-(heptafluoroiso-propyl)phenyl |
| 711 | 4-cyanophenyl | Me | F | H | 2-bromo-4-(heptafluoroiso-propyl)phenyl |
| 712 | 2-chloropyridin-3-yl | Me | F | H | 2-bromo-4-(heptafluoroiso-propyl)phenyl |
| 713 | phenyl | Me | F | H | 2-iodo-4-(heptafluoroiso-propyl)phenyl |
| 714 | 2-fluorophenyl | Me | F | H | 2-iodo-4-(heptafluoroiso-propyl)phenyl |
| 715 | 4-fluorophenyl | Me | F | H | 2-iodo-4-(heptafluoroiso-propyl)phenyl |
| 716 | 4-nitrophenyl | Me | F | H | 2-iodo-4-(heptafluoroiso-propyl)phenyl |
| 717 | 4-cyanophenyl | Me | F | H | 2-iodo-4-(heptafluoroiso-propyl)phenyl |
| 718 | 2-chloropyridin-3-yl | Me | F | H | 2-iodo-4-(heptafluoroiso-propyl)phenyl |
| 719 | phenyl | Me | F | H | 2-iodo-4-(heptafluoroiso-propyl)phenyl |
| 720 | 2-fluorophenyl | Me | F | H | 2-iodo-4-(heptafluoroiso-propyl)phenyl |
| 721 | 4-fluorophenyl | Me | F | H | 2-iodo-4-(heptafluoroiso-propyl)phenyl |
| 722 | 4-nitrophenyl | Me | F | H | 2-iodo-4-(heptafluoroiso-propyl)phenyl |
| 723 | 4-cyanophenyl | Me | F | H | 2-iodo-4-(heptafluoroiso-propyl)phenyl |
| 724 | 2-chloropyridin-3-yl | Me | F | H | 2-iodo-4-(heptafluoroiso-propyl)phenyl |
| 725 | phenyl | Me | F | H | 2-trifluoromethylthio-4-(hepta-fluoroisopropyl)phenyl |
| 726 | 2-fluorophenyl | Me | F | H | 2-trifluoromethylthio-4-(hepta-fluoroisopropyl)phenyl |
| 727 | 4-fluorophenyl | Me | F | H | 2-trifluoromethylthio-4-(hepta-fluoroisopropyl)phenyl |
| 728 | 4-nitrophenyl | Me | F | H | 2-trifluoromethylthio-4-(hepta-fluoroisopropyl)phenyl |
| 729 | 4-cyanophenyl | Me | F | H | 2-trifluoromethylthio-4-(hepta-fluoroisopropyl)phenyl |
| 730 | 2-chloropyridin-3-yl | Me | F | H | 2-trifluoromethylthio-4-(hepta-fluoroisopropyl)phenyl |
| 731 | phenyl | Et | H | H | 2-trifluoromethyl-4-(hepta-fluoroisopropyl)phenyl |
| 732 | phenyl | Me | MeO | H | 2-trifluoromethylthio-4-(hepta-fluoroisopropyl)phenyl |
| 733 | 2-fluorophenyl | Me | MeO | H | 2-trifluoromethylthio-4-(hepta-fluoroisopropyl)phenyl |
| 734 | 4-fluorophenyl | Me | MeO | H | 2-trifluoromethylthio-4-(hepta-fluoroisopropyl)phenyl |
| 735 | 4-nitrophenyl | Me | MeO | H | 2-trifluoromethylthio-4-(hepta-fluoroisopropyl)phenyl |
| 736 | 4-cyanophenyl | Me | MeO | H | 2-trifluoromethylthio-4-(hepta-fluoroisopropyl)phenyl |
| 737 | 2-chloropyridin-3-yl | Me | MeO | H | 2-trifluoromethylthio-4-(hepta-fluoroisopropyl)phenyl |
| 738 | phenyl | Me | F | cyano | 2-trifluoromethylthio-4-(hepta-fluoroisopropyl)phenyl |
| 739 | 2-fluorophenyl | Me | F | cyano | 2-trifluoromethylthio-4-(hepta-fluoroisopropyl)phenyl |
| 740 | 4-fluorophenyl | Me | F | cyano | 2-trifluoromethylthio-4-(hepta-fluoroisopropyl)phenyl |
| 741 | 4-nitrophenyl | Me | F | cyano | 2-trifluoromethylthio-4-(hepta-fluoroisopropyl)phenyl |
| 742 | 4-cyanophenyl | Me | F | cyano | 2-trifluoromethylthio-4-(hepta-fluoroisopropyl)phenyl |
| 743 | 2-chloropyridin-3-yl | Me | F | cyano | 2-trifluoromethylthio-4-(hepta-fluoroisopropyl)phenyl |
| 744 | phenyl | Me | F | nitro | 2-trifluoromethylthio-4-(hepta-fluoroisopropyl)phenyl |
| 745 | 2-fluorophenyl | Me | F | nitro | 2-trifluoromethylthio-4-(hepta-fluoroisopropyl)phenyl |
| 746 | 4-fluorophenyl | Me | F | nitro | 2-trifluoromethylthio-4-(hepta-fluoroisopropyl)phenyl |
| 747 | 4-nitrophenyl | Me | F | nitro | 2-trifluoromethylthio-4-(hepta-fluoroisopropyl)phenyl |

TABLE 5-continued

| Compound No. | Q¹ | R¹ | X¹ | X² | Q² |
|---|---|---|---|---|---|
| 748 | 4-cyanophenyl | Me | F | nitro | 2-trifluoromethylthio-4-(heptafluoroisopropyl)phenyl |
| 749 | 2-chloropyridin-3-yl | Me | F | nitro | 2-trifluoromethylthio-4-(heptafluoroisopropyl)phenyl |
| 750 | phenyl | Me | H | cyano | 2-trifluoromethylthio-4-(heptafluoroisopropyl)phenyl |
| 751 | 2-fluorophenyl | Me | H | cyano | 2-trifluoromethylthio-4-(heptafluoroisopropyl)phenyl |
| 752 | 4-fluorophenyl | Me | H | cyano | 2-trifluoromethylthio-4-(heptafluoroisopropyl)phenyl |
| 753 | 4-nitrophenyl | Me | H | cyano | 2-trifluoromethylthio-4-(heptafluoroisopropyl)phenyl |
| 754 | 4-cyanophenyl | Me | H | cyano | 2-trifluoromethylthio-4-(heptafluoroisopropyl)phenyl |
| 755 | 2-chloropyridin-3-yl | Me | H | cyano | 2-trifluoromethylthio-4-(heptafluoroisopropyl)phenyl |
| 756 | phenyl | Me | H | nitro | 2-trifluoromethylthio-4-(heptafluoroisopropyl)phenyl |
| 757 | 2-fluorophenyl | Me | H | nitro | 2-trifluoromethylthio-4-(heptafluoroisopropyl)phenyl |
| 758 | 4-fluorophenyl | Me | H | nitro | 2-trifluoromethylthio-4-(heptafluoroisopropyl)phenyl |
| 759 | 4-nitrophenyl | Me | H | nitro | 2-trifluoromethylthio-4-(heptafluoroisopropyl)phenyl |
| 760 | 4-cyanophenyl | Me | H | nitro | 2-trifluoromethylthio-4-(heptafluoroisopropyl)phenyl |
| 761 | 2-chloropyridin-3-yl | Me | H | nitro | 2-trifluoromethylthio-4-(heptafluoroisopropyl)phenyl |

The alkylated aromatic amide derivatives represented by Formula (4), which are obtained by the method for producing an alkylated aromatic amide derivative of the invention, are extremely useful production intermediates in the method for producing an amide derivative that exhibits excellent efficacy in terms of pet controlling effects.

EXAMPLES

Hereinafter, the present invention is further explained in detail with reference to Examples; however it should be construed that the invention is by no means limited thereto.

Note that, unless otherwise specifically stated, the chemical shift values of $^1$H-NMR are expressed at the lower magnetic field side, on the basis of tetramethylsilane, in ppm unit. "s" means a singlet, "d" means a doublet, "t" means a triplet, "m" means a multiplet, and "brs" means a broad singlet. Further, unless otherwise specifically stated "%" is based on mass.

Synthesis Example 1

Production of 2-Fluoro-3-(N-methylbenzamido)-N-(2-(trifluoromethyl)phenyl)benzamide 26.8 g (166.3 mmol) of 2-(trifluoromethyl)aniline, 37.0 g (365.9 mmol) of triethylamine, and 100.9 g (365.9 mmol) of 2-fluoro-3-(N-methylbenzamido)benzoyl chloride were added to tetrahydrofuran (400 mL), and the mixture was stirred at 50° C. for 3 hours. The reaction liquid was filtered through a filter, and an aqueous solution (125 mL) containing 14.6 g (365.9 mmol) of sodium hydroxide was added to the filtrate, followed by stirring at 50° C. for 30 minutes. After the solvent was distilled off under reduced pressure, the obtained residue was extracted with ethyl acetate, and washed with aqueous potassium carbonate solution and saturated saline solution, sequentially. The organic layer was dried over magnesium sulfate. Then, magnesium sulfate was filtered off, and the solvent was distilled off under reduced pressure. The obtained solid was washed with n-hexane and isopropyl ether, followed by drying, to obtain 63.2 g (yield 91%) of the title compound as a white solid.

$^1$H-NMR (DMSO-$d_6$, 70° C., δ ppm) 9.81 (1H, s), 7.80-7.69 (2H, m), 7.62-7.49 (4H, m), 7.33-7.21 (6H, m), 3.33 (3H, s).

Example 1

Production of 2-Fluoro-3-(N-methylbenzamido)-N-(2-(trifluoromethyl)-4-(heptafluoroisopropyl)phenyl)benzamide 0.8 g (20 mmol) of powdery sodium hydroxide and 0.93 g (3.3 mmol) of iron(II) sulfate heptahydrate were stirred in an ice bath, until the color of the mixture changed to black. Immediately after the discoloration, 5 g of N,N-dimethylformamide were added thereto, and then, a solution obtained by dissolving 1 g (2.4 mmol) of 2-fluoro-3-(N-methylbenazmido)-N-(2-(trifluoromethyl)phenyl)benzamide and 1 g (3.4 mmol) of heptafluoroisopropyl iodide in 5 g of N,N-dimethylformamide was added thereto, followed by stirring at room temperature for 3 hours. The obtained reaction liquid was filtered through cerite and the residue was washed with 50 mL of ethyl acetate. Then, 40 g of water were added to the resulting reaction liquid, and after performing extraction, the organic layer was dried over magnesium sulfate. Then, magnesium sulfate was filtered off, and the solvent was distilled off under reduced pressure. Thereafter, the condensed residue was purified by silica gel chromatography, to obtain 0.89 g (yield 63%) of the title compound as a white solid.

$^1$H-NMR (CDCl$_3$, δ ppm) 8.86 (1H, d, J=8.9 Hz), 8.68 (1H, d, J=8.3 Hz), 8.01 (1H, s), 7.88-7.84 (2H, m), 7.36-7.29 (7H, m), 3.48 (3H, s).

Example 2

Production of 2-Fluoro-3-(N-methylbenzamido)-N-(2-bromo-4-(heptafluoroisopropyl)-6-(trifluoromethyl)phenyl)benzamide 4 g of N,N-dimethylformamide and 1 g (1.72 mmol) of 2-fluoro-3-(N-methylbenzamido)-N-(2-(trifluoromethyl)-4-(heptafluoroisopropyl)phenyl)benzamide obtained as described in the above were added to 68.5 mg (1.71 mmol) of sodium hydride (60% product), and the mixture was stirred in an ice bath for 10 minutes. 0.31 g (1.80 mmol) of N-bromosuccinimide were added to the reaction solution, and the mixture was stirred at room temperature for 2 hours. Water was added to the reaction solution, followed by performing extraction with ethyl acetate, and, thereafter, the organic layer was dried over magnesium sulfate. Then, magnesium sulfate was filtered off, and the solvent was distilled off under reduced pressure. Thereafter, the condensed residue was purified by silica gel chromatography, to obtain 0.93 g (yield 82%) of the title compound as a white solid.

$^1$H-NMR (CDCl$_3$, ppm) δ 8.13 (1H, s), 7.97-8.06 (2H, m), 7.90 (1H, s) 7.43-7.45 (1H, m), 6.99-7.33 (6H, m), 3.50 (3H, s).

Example 2-1

Production of 2-Fluoro-3-(N-methylbenzamido)-N-(2-bromo-4-(heptafluoroisopropyl)-6-(trifluoromethyl)phenyl)benzamide 5 g of N,N-dimethylformamide and 1 g (1.72 mmol) of 2-fluoro-3-(N-methylbenzamido)-N-(2-(trifluoromethyl)-4-(heptafluoroisopropyl)phenyl)benzamide obtained as described in the above were added to 140 mg (3.42 mmol) of sodium hydride, and the mixture was stirred under room temperature for 10 minutes. 0.34 g (1.90 mmol) of N-bromosuccinimide were added to the reaction liquid, and the resulting mixture stirred at room temperature for 2 hours. Water was added to the reaction liquid, followed by performing extraction with ethyl acetate, and thereafter, the organic layer was dried over magnesium sulfate. Then, magnesium sulfate was filtered off, and the solvent was distilled off under reduced pressure. Thereafter, the condensed residue was purified by silica gel chromatography, to obtain 0.64 g (yield 56%) of the title compound as a white solid.

Example 3

Production of 3-Nitro-N-(2-(trifluoromethyl)-4-(heptafluoroisopropyl)phenyl)benzamide 1.1 g (27 mmol) of powdery sodium hydroxide and 1.2 g (4.5 mmol) of iron(II) sulfate heptahydrate were stirred in an ice bath, until the color of the mixture changed to black. Immediately after the discoloration, 5 g of N,N-dimethylformamide were added thereto, and then, a solution obtained by dissolving 1.0 g (3.2 mmol) of 3-nitro-N-(2-(trifluoromethyl)phenyl)benzamide and 1.3 g (4.5 mmol) of heptafluoroisopropyl iodide in 5 g of N,N-dimethylformamide was added thereto, followed by stirring at room temperature for 3 hours. The obtained reaction liquid was filtered through cerite and the residue was washed with 50 mL of ethyl acetate. Then, 40 g of water were added to the resulting reaction liquid, and after performing extraction, the organic layer was dried over magnesium sulfate. Then, magnesium sulfate was filtered off, and the solvent was distilled off under reduced pressure. Thereafter, the condensed residue was purified by silica gel chromatography, to obtain 0.44 g (yield 28%) of the title compound as a red solid.

$^1$H-NMR (DMSO-d$_6$, δ ppm) 10.82 (1H*⅘, brs), 10.71 (1H*⅕, brs), 8.77 (1H*⅘, t, J=1.8 Hz), 8.73 (1H*⅕, t, J=2.0 Hz), 8.50-8.46 (1H, m), 8.37-8.34 (1H, m), 8.21-8.20 (1*⅕H, m), 8.14-8.12 (1*⅘H, m), 7.96-7.94 (2H, m), 7.90-7.85 (1H, m).

Example 4

Production of 3-Cyano-N-(2-(trifluoromethyl)-4-(heptafluoroisopropyl)phenyl)benzamide 1.1 g (29 mmol) of powdery sodium hydroxide and 1.3 g (4.8 mmol) of iron(II) sulfate heptahydrate were stirred in an ice bath, until the color of the mixture changed to black. Immediately after the discoloration, 5 g of N,N-dimethylformamide were added thereto, and then, a solution obtained by dissolving 1.0 g (3.5 mmol) of 3-cyano-N-(2-(trifluoromethyl)phenyl)benzamide and 1.4 g (4.8 mmol) of heptafluoroisopropyl iodide in 5 g of N,N-dimethylformamide was added thereto, followed by stirring at room temperature for 3 hours. The obtained reaction liquid was filtered through cerite and the residue was washed with 50 mL of ethyl acetate. Then, 40 g of water were added to the resulting reaction liquid, and after performing extraction, the organic layer was dried over magnesium sulfate. Then, magnesium sulfate was filtered off, and the solvent was distilled off under reduced pressure. Thereafter, the condensed residue was purified by silica gel chromatography, to obtain 0.93 g (yield 59%) of the title compound as a white solid.

$^1$H-NMR (DMSO-d$_6$, δ ppm) 10.64 (1H*⅘, brs), 10.51 (1H*⅕, brs), 8.36 (1H*⅘, s), 8.30 (1H*⅕, s), 8.23-8.20 (1H, m), 8.13-8.04 (2H, m), 7.94-7.89 (2H, m), 7.79-7.78 (1H, m).

Example 5

Production of 2-Fluoro-3-(N-methylbenzamido)-N-(2-methyl-4-(heptafluoroisopropyl)phenyl)benzamide 0.55 g (14 mmol) of powdery sodium hydroxide and 0.64 g (2.3 mmol) of iron(II) sulfate heptahydrate were stirred in an ice bath, until the color of the mixture changed to black. Immediately after the discoloration, 3 g of N,N-dimethylformamide were added thereto, and then, a solution obtained by dissolving 0.60 g (1.7 mmol) of 2-fluoro-3-(N-methylbenzamido)-N-(2-methyl-phenyl)benzamide and 0.68 (2.3 mmol) of heptafluoroisopropyl iodide in 3 g of N,N-dimethylformamide was added thereto, followed by stirring at room temperature for 3 hours. The obtained reaction liquid was filtered through cerite and the residue was washed with 50 mL of ethyl acetate. Then, 40 g of water were added to the resulting reaction liquid, and after performing extraction, the organic layer was dried over magnesium sulfate. Then, magnesium sulfate was filtered off, and the solvent was distilled off under reduced pressure. Thereafter, the condensed residue was purified by silica gel chromatography, to obtain 0.26 g (yield 30%) of the title compound as a white solid.

$^1$H-NMR (CDCl$_3$, δ ppm) 8.35 (1H, d, J=8.6 Hz), 8.03-8.01 (1H, m), 7.49 (1H, d, J=9.2 Hz), 7.43-7.37 (4H, m), 7.26-7.22 (5H, m), 3.49 (3H, s), 2.34 (3H, s).

Example 6

Production of 2-Fluoro-3-(N-methylbenzamido)-N-(2-bromo-4-(heptafluoroisopropyl)phenyl)benzamide 0.47 g (12 mmol) of powdery sodium hydroxide and 0.54 g (1.9 mmol) of iron(II) sulfate heptahydrate were stirred in an ice bath, until the color of the mixture changed to black. Immediately after the discoloration, 3 g of N,N-dimethylformamide were added thereto, and then, a solution obtained by dissolving 0.60 g (1.4 mmol) of 2-fluoro-3-(N-methylbenzamido)-N-(2-bromo-phenyl)benzamide and 0.57 g (1.9 mmol) of heptafluoroisopropyl iodide in 3 g of N,N-dimethylformamide was added thereto, followed by stirring at room temperature for 3 hours. The obtained reaction liquid was filtered through cerite and the residue was washed with 50 mL of ethyl acetate. Then, 40 g of water were added to the resulting reaction liquid, and after performing extraction, the organic layer was dried over magnesium sulfate. Then, magnesium sulfate was filtered off, and the solvent was distilled off under reduced pressure. Thereafter, the condensed residue was purified by silica gel chromatography, to obtain 0.092 g (yield 11%) of the title compound as a white solid.

$^1$H-NMR (CDCl$_3$, δ ppm) 8.97 (1H, brs), 8.70 (1H, d, J=8.9 Hz), 8.01 (1H, t, J=6.9 Hz), 7.84 (1H, d, J=1.8 Hz), 7.60-7.59 (1H, m), 7.40-7.36 (3, m), 7.29-7.22 (4H, m), 3.50 (3H, s).

As described above, the aimed alkylated aromatic amide derivative can be obtained in a short step, by the method for producing an alkylated aromatic amide derivative of the invention.

The disclosure of Japanese Patent Application No. 2012-085053 is incorporated by reference herein in its entirety.

All publications, patent applications, and technical standards mentioned in this specification are herein incorporated by reference to the same extent as if such individual publication, patent application, or technical standard was specifically and individually indicated to be incorporated by reference.

The invention claimed is:

1. A method for producing an alkylated aromatic amide of the following Formula (4), the method comprising a process of allowing an aromatic amide of the following Formula (1) and a haloalkyl compound of the following Formula (3) to react with each other in the presence of a base and a metal salt selected from the group consisting of iron metal salts showing a valency of two, copper metals showing a valency of one, and samarium (II) iodide:

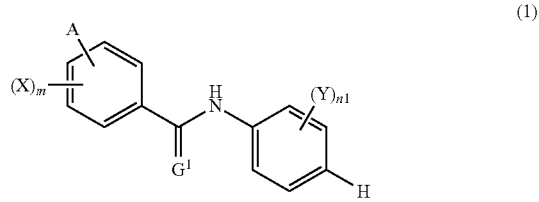

(1)

wherein, in Formula (1), each X is a hydrogen atom, a halogen atom, a nitro group, a cyano group, a C1-C4 alkoxy group, or a dimethylamino group;
m is an integer from 1 to 4, and n1 is an integer from 1 to 4;
G$^1$ is an oxygen atom or a sulfur atom;
Y is a hydrogen atom, a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, or an acetylamino group;

A is a hydrogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, a C1-C4 alkylaminocarbonyl group, a methylsulfinyl C1-C4-alkylamino-carbonyl group, a methylsulfonyl C1-C4-alkylamino-carbonyl group, an acetylamino group, or an unsubstituted phenyl group, or a phenyl group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group, or an unsubstituted heterocyclic group, or a heterocyclic group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group, or a group of the following Formula (2):

(2)

wherein, in Formula (2), $G^2$ is an oxygen atom or a sulfur atom;

$R^1$ is a hydrogen atom, a C1-C6 alkyl group, or a C1-C6 haloalkyl group; and $Q^1$ is a C1-C6 alkyl group, a C1-C6 haloalkyl group, or an unsubstituted phenyl group, or a phenyl group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group, or an unsubstituted heterocyclic group, or a heterocyclic group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group; and the heterocyclic group in A of Formula (1) and in $Q^1$ of Formula (2) is a pyridyl group, a pyridin-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group, or a tetrazolyl group:

$$Z^1\text{—Xa} \quad (3)$$

wherein, in Formula (3), $Z^1$ is a C1-C6 alkyl group or a C1-C4 haloalkyl group; and Xa is an iodine atom or a bromine atom:

(4)

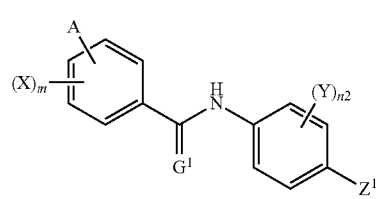

wherein, in Formula (4), n2 is an integer from 1 to 4; $Z^1$ has the same definition as $Z^1$ in Formula (3), and X, m, $G^1$, Y, and A have the same definitions as X, m, $G^1$, Y, and A in Formula (1), respectively.

2. The production method according to claim 1, wherein the aromatic amide of Formula (1) is an aromatic amide of the following Formula (5) and the alkylated aromatic amide of Formula (4) is an alkylated aromatic amide of the following Formula (6):

(5)

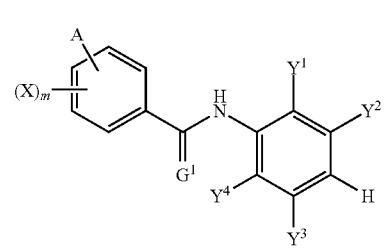

wherein, in Formula (5), each of $Y^1$, $Y^2$, $Y^3$, and $Y^4$ is a hydrogen atom, a halogen atom, a C1-C6 alkyl group, a C1-C6 haloalkyl group, a C1-C4 alkylthio group, a C1-C4 haloalkylthio group, a C1-C4 alkylsulfinyl group, a C1-C4 haloalkylsulfinyl group, a C1-C4 alkylsulfonyl group, or a C1-C4 haloalkylsulfonyl group;

and X, m, $G^1$, and A have the same definitions as X, m, $G^1$, and A in Formula (1), respectively:

(6)

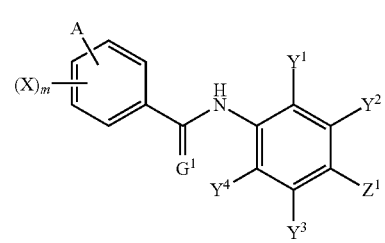

wherein, in Formula (6), $Z^1$ has the same definition as $Z^1$ in Formula (3); and $Y^1$, $Y^2$, $Y^3$, $Y^4$, X, m, $G^1$, and A have the same definitions as $Y^1$, $Y^2$, $Y^3$, $Y^4$, X, m, $G^1$, and A in Formula (5), respectively.

3. The production method according to claim 2, wherein the aromatic amide of Formula (5) is an aromatic amide of the following Formula (7) and the alkylated aromatic amide of Formula (6) is an alkylated aromatic amide of the following Formula (8):

(7)

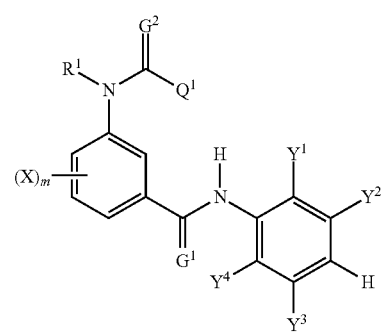

wherein, in Formula (7), $G^2$, $Q^1$, and $R^1$ have the same definitions as $G^2$, $Q^1$, and $R^1$ in Formula (2), respectively; and X, m, $G^1$, $Y^1$, $Y^2$, $Y^3$, and $Y^4$ have the same definitions as X, m, $G^1$, $Y^1$, $Y^2$, $Y^3$, and $Y^4$ in Formula (5) above, respectively:

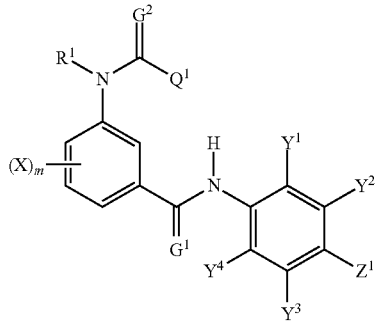
(8)

wherein, in Formula (8), $Z^1$ has the same definition as $Z^1$ in Formula (3); and $Y^1$, $Y^2$, $Y^3$, $Y^4$, X, m, $G^1$, $G^2$, $Q^1$, and $R^1$ have the same definitions as $Y^1$, $Y^2$, $Y^3$, $Y^4$, X, m, $G^1$, $G^2$, $Q^1$, and $R^1$ in Formula (7), respectively.

4. A method for producing a halogenated aromatic amide of the following Formula (10), the method comprising:
a process of obtaining an alkylated aromatic amide of Formula (8) by the production method according to claim 3, and
a process of halogenating the alkylated aromatic amide of Formula (8) under a basic condition:

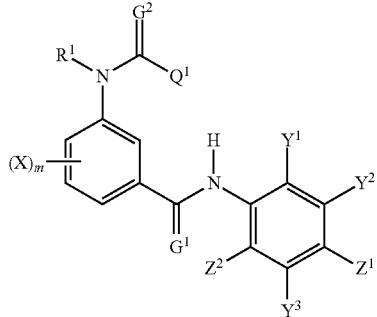
(10)

wherein, in Formula (10), $Z^2$ is a halogen atom; and X, m, $G^1$, $G^2$, $Q^1$, $R^1$, $Y^1$, $Y^2$, $Y^3$, and $Z^1$ have the same definitions as X, m, $G^1$, $G^2$, $Q^1$, $R^1$, $Y^1$, $Y^2$, $Y^3$, and $Z^1$ in Formula (8), respectively; and
wherein, in Formula (8), $Y^4$ is a hydrogen atom.

5. An aromatic amide of the following Formula (7):

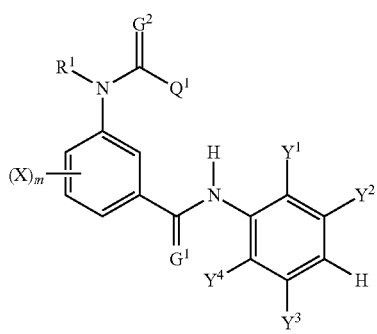
(7)

wherein, in Formula (7), each X is a hydrogen atom, a halogen atom, a nitro group, a cyano group, a C1-C4 alkoxy group, or a dimethylamino group;
m is an integer from 1 to 4;
each of $G^1$ and $G^2$ is an oxygen atom;
$Y^1$ is a hydrogen atom, a fluorine atom, a bromine atom, an iodine atom, a C1-C6 alkyl group, a C1-C6 haloalkyl group, a C1-C4 alkylthio group, a C1-C4 haloalkylthio group, a C1-C4 alkylsulfinyl group, a C1-C4 haloalkylsulfinyl group, a C1-C4 alkylsulfonyl group, or a C1-C4 haloalkylsulfonyl group, each of $Y^2$ and $Y^3$ is a hydrogen atom, a halogen atom, a C1-C6 alkyl group, or a C1-C6 haloalkyl group, $Y^4$ is a hydrogen atom, a fluorine atom, a bromine atom, an iodine atom, a C1-C6 alkyl group, a C1-C6 haloalkyl group, a C1-C4 alkylthio group, a C1-C4 haloalkylthio group, a C1-C4 alkylsulfinyl group, a C1-C4 haloalkylsulfinyl group, a C1-C4 alkylsulfonyl group, or a C1-C4 haloalkylsulfonyl group, provided that at least one of $Y^1$ or $Y^4$ is not a hydrogen atom;
$R^1$ is a C1-C6 alkyl group or a C1-C6 haloalkyl group;
$Q^1$ is a C1-C6 alkyl group, a C1-C6 haloalkyl group, or
an unsubstituted phenyl group, or a phenyl group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsufonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group, or
an unsubstituted heterocyclic group, or a heterocyclic group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group; and
the heterocyclic group is a pyridyl group, a pyridin-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group, or a tetrazolyl group.

6. An alkylated aromatic amide of the following Formula (9):

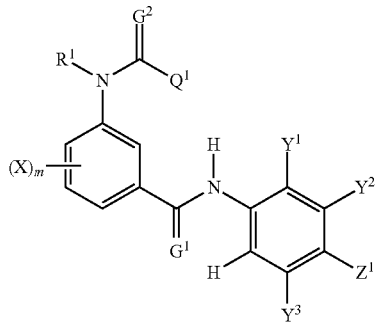

wherein, in Formula (9), each X is a fluorine atom, a bromine atom, an iodine atom, a nitro group, a cyano group, a C1-C4 alkoxy group, or a dimethylamino group;
m is an integer from 1 to 3;
each of $G^1$ and $G^2$ is an oxygen atom;
each of $Y^1$, $Y^2$, and $Y^3$ is a hydrogen atom, a halogen atom, a C1-C6 alkyl group, a C1-C6 haloalkyl group, a C1-C4 alkylthio group, a C1-C4 haloalkylthio group, a C1-C4 alkylsulfinyl group, a C1-C4 haloalkylsulfinyl group, a C1-C4 alkylsulfonyl group, or a C1-C4 haloalkylsulfonyl group;
$Z^1$ is a C1-C6 haloalkyl group;
$R^1$ is a C1-C6 alkyl group or a C1-C6 haloalkyl group;
$Q^1$ is a C1-C6 haloalkyl group, or
an unsubstituted phenyl group, or a phenyl group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group, or
an unsubstituted heterocyclic group, or a heterocyclic group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group; and
the heterocyclic group is a pyridyl group, a pyridin-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group, or a tetrazolyl group.

7. The alkylated aromatic amide according to claim 6, wherein, in Formula (9), $Y^1$ is a C1-C2 haloalkyl group, each of $Y^2$ and $Y^3$ is a hydrogen atom, $Z^1$ is a C1-C6 fluoroalkyl group, and X is a halogen atom.

8. An aromatic amide of the following Formula (7'):

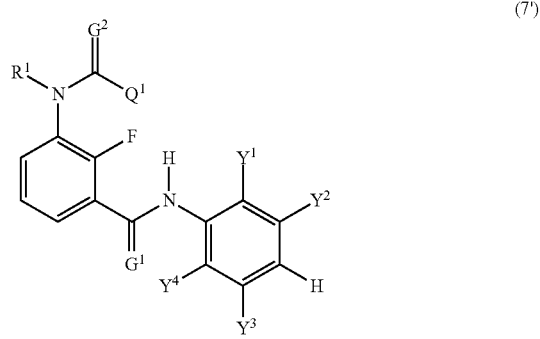

wherein, in Formula (7'), each of $G^1$ and $G^2$ is an oxygen atom;
$Y^1$ is a hydrogen atom, a fluorine atom, a bromine atom, an iodine atom, a C1-C6 alkyl group, a C1-C6 haloalkyl group, a C1-C4 alkylthio group, a C1-C4 haloalkylthio group, a C1-C4 alkylsulfinyl group, a C1-C4 haloalkylsulfinyl group, a C1-C4 alkylsulfonyl group, or a C1-C4 haloalkylsulfonyl group, each of $Y^2$ and $Y^3$ is a hydrogen atom, a halogen atom, a C1-C6 alkyl group, or a C1-C6 haloalkyl group, $Y^4$ is a hydrogen atom, a fluorine atom, a bromine atom, an iodine atom, a C1-C6 alkyl group, a C1-C6 haloalkyl group, a C1-C4 alkylthio group, a C1-C4 haloalkylthio group, a C1-C4 alkylsulfinyl group, a C1-C4 haloalkylsulfinyl group, a C1-C4 alkylsulfonyl group, or a C1-C4 haloalkylsulfonyl group, provided that at least one of $Y^1$ or $Y^4$ is not a hydrogen atom;
$R^1$ is a hydrogen atom, a C1-C6 alkyl group, or a C1-C6 haloalkyl group;
$Q^1$ is a C1-C6 alkyl group, a C1-C6 haloalkyl group, or
an unsubstituted phenyl group, or a phenyl group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsufonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group, or an unsubstituted heterocyclic group, or a heterocyclic group having one or more substituents, which may be the same or different, selected from the group consisting of a halogen atom, a C1-C6 alkyl group, a C1-C6 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, an arylsulfonyl group, a C1-C4 alkylamino group, a di-C1-C4-alkylamino group, a cyano group, a nitro group, a hydroxyl group, a C1-C4 alkylcarbonyl group, a C1-C4 haloalkylcarbonyl group, a C1-C4 alkylcarbonyloxy group, a C1-C4 alkoxycarbonyl group, an acetylamino group, and a phenyl group; and the heterocyclic group is a pyridyl group, a pyridin-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group, or a tetrazolyl group.

9. The alkylated aromatic amide according to claim 7, wherein, in Formula (9), $Y^1$ is a trifluoromethyl group, each of $Y^2$ and $Y^3$ is a hydrogen atom, $Z^1$ is a heptafluoroisopropyl group, and X is a halogen atom.

* * * * *